(12) United States Patent
Milstein et al.

(10) Patent No.: US 6,627,228 B1
(45) Date of Patent: Sep. 30, 2003

(54) POLYMERIC DELIVERY AGENTS AND DELIVERY AGENTS COMPOUNDS

(75) Inventors: Sam J. Milstein, Larchmont, NY (US); Eugene N. Barantsevitch, Scarsdale, NY (US); Nai Fang Wang, Long Island City, NY (US); Jun Liao, Tarrytown, NY (US); John E. Smart, Katonah, NY (US); Richard D. Conticello, Ossining, NY (US); Raphael M. Ottenbrite, Midlothian, VA (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 09/889,005
(22) PCT Filed: Jan. 7, 2000
(86) PCT No.: PCT/US00/00476
§ 371 (c)(1), (2), (4) Date: Oct. 10, 2001
(87) PCT Pub. No.: WO00/40203
PCT Pub. Date: Jul. 13, 2000

Related U.S. Application Data
(60) Provisional application No. 60/115,273, filed on Jan. 8, 1999.

(51) Int. Cl.$^7$ .................. A61K 9/14; A61K 31/785; A61K 9/48; A61K 9/20
(52) U.S. Cl. ............... 424/489; 424/78.16; 424/451; 424/452; 424/464; 424/465
(58) Field of Search ............... 424/78.16, 451, 424/452, 464, 465, 489; 514/553, 561

(56) References Cited

U.S. PATENT DOCUMENTS

| | | | |
|---|---|---|---|
| 4,147,767 A | 4/1979 | Yapel | 424/22 |
| 4,238,506 A | 12/1980 | Stach et al. | 424/319 |
| 4,692,433 A | 9/1987 | Hostetler et al. | 514/12 |
| 4,757,066 A | 7/1988 | Shiokari et al. | 514/210 |
| 4,873,087 A | 10/1989 | Morishita et al. | 424/433 |
| 4,895,725 A | 1/1990 | Kantor et al. | 424/455 |
| 4,925,673 A | 5/1990 | Steiner | |
| 4,976,968 A | 12/1990 | Steiner | 424/491 |
| 4,983,402 A | 1/1991 | Steiner | 424/491 |
| 5,066,487 A | 11/1991 | Morelle et al. | 424/68 |
| 5,328,992 A | 7/1994 | Peter et al. | 534/16 |
| 5,352,461 A | 10/1994 | Feldstein et al. | 424/493 |
| 5,401,516 A | 3/1995 | Milstein et al. | 424/491 |
| 5,443,841 A | 8/1995 | Milstein et al. | 424/451 |
| 5,447,728 A | 9/1995 | Milstein et al. | 424/490 |
| 5,451,410 A | 9/1995 | Milstein et al. | 424/490 |
| 5,455,335 A | 10/1995 | Kahane et al. | 536/5 |
| 5,540,939 A | 7/1996 | Milstein et al. | 424/491 |
| 5,541,155 A | 7/1996 | Leone-Bay et al. | 514/2 |
| 5,578,323 A | 11/1996 | Milstein et al. | 424/499 |
| 5,601,846 A | 2/1997 | Milstein et al. | 424/499 |
| 5,629,020 A | 5/1997 | Leone-Bay et al. | 424/489 |
| 5,643,957 A | 7/1997 | Leone-Bay et al. | 514/563 |
| 5,650,386 A | 7/1997 | Leone-Bay et al. | 514/2 |
| 5,667,806 A | 9/1997 | Kantor et al. | 424/484 |
| 5,693,338 A | 12/1997 | Milstein et al. | 424/451 |
| 5,705,529 A | 1/1998 | Matyus et al. | 514/541 |
| 5,709,861 A | 1/1998 | Santiago et al. | 424/184 |
| 5,714,167 A * | 2/1998 | Milstein et al. | 424/490 |
| 5,750,147 A | 5/1998 | Kantor et al. | 424/491 |
| 5,766,633 A | 6/1998 | Milstein et al. | 424/489 |
| 5,773,647 A | 6/1998 | Leone-Bay et al. | 562/444 |
| RE35,862 E | 7/1998 | Steiner et al. | 424/455 |
| 5,776,888 A | 7/1998 | Leone-Bay et al. | 514/2 |
| 5,792,451 A | 8/1998 | Sarubbi et al. | 424/85.4 |
| 5,804,688 A | 9/1998 | Leone-Bay et al. | 562/444 |
| 5,811,127 A | 9/1998 | Milstein et al. | 424/490 |
| 5,820,881 A | 10/1998 | Milstein et al. | 424/489 |
| 5,824,345 A | 10/1998 | Milstein et al. | 424/489 |
| 5,840,340 A | 11/1998 | Milstein et al. | 424/499 |
| 5,863,944 A | 1/1999 | Leone-Bay et al. | 514/559 |
| 5,866,536 A | 2/1999 | Leone-Bay et al. | 514/2 |
| 5,876,710 A | 3/1999 | Leone-Bay et al. | 424/85.1 |
| 5,879,681 A | 3/1999 | Leone-Bay et al. | 424/85.1 |
| 5,935,601 A | 8/1999 | Leone-Bay et al. | 424/489 |
| 5,939,381 A | 8/1999 | Leone-Bay et al. | 514/2 |
| 5,955,503 A | 9/1999 | Leone-Bay et al. | 514/563 |
| 5,958,457 A | 9/1999 | Santiago et al. | 424/490 |
| 5,962,710 A | 10/1999 | Gschneidner et al. | 554/112 |
| 5,965,121 A | 10/1999 | Leone-Bay et al. | 424/85.2 |
| 5,972,387 A | 10/1999 | Milstein et al. | 424/491 |
| 5,976,569 A | 11/1999 | Milstein et al. | 424/451 |
| 5,989,539 A | 11/1999 | Leone-Bay et al. | 424/85.2 |
| 5,990,166 A | 11/1999 | Leone-Bay et al. | 514/563 |
| 6,001,347 A | 12/1999 | Leone-Bay et al. | 424/85.1 |
| 6,051,258 A | 4/2000 | Kantor | 424/491 |
| 6,051,561 A | 4/2000 | Leone-Bay et al. | 514/56 |
| 6,060,513 A | 5/2000 | Leone-Bay et al. | 514/559 |
| 6,071,510 A | 6/2000 | Leone-Bay et al. | 424/85.2 |
| 6,071,538 A | 6/2000 | Milstein et al. | 424/464 |
| 6,084,112 A | 7/2000 | Ho et al. | 554/114 |
| 6,090,958 A | 7/2000 | Leone-Bay et al. | 554/112 |
| 6,099,856 A | 8/2000 | Milstein et al. | 424/450 |
| 6,100,285 A | 8/2000 | Kantor | 514/400 |
| 6,100,298 A | 8/2000 | Leone-Bay et al. | 514/563 |
| 6,180,140 B1 | 1/2001 | Leone-Bay et al. | 424/489 |
| 6,221,367 B1 | 4/2001 | Milstein et al. | 424/400 |

FOREIGN PATENT DOCUMENTS

| | | | |
|---|---|---|---|
| EP | 0036145 | 9/1981 | |
| ES | 369853 | 7/1969 | |
| GB | 2095994 | 10/1982 | |
| WO | WO 96/12473 | * 5/1996 | |
| WO | 96/12473 | 5/1996 | ............. A61K/9/16 |
| WO | 96/30036 | 10/1996 | .......... A61K/38/00 |
| WO | WO 96/30036 | * 10/1996 | |
| WO | 99/55376 | 11/1999 | .......... A61K/47/48 |

OTHER PUBLICATIONS

Haas, S., et al., S.T.P. Pharma Sciences, 1998; 8(1)59–65.
Leone–Bay, A., et al., J. Controlled Release, 1998; 50:41–49.
Leone–Bay, A., et al., J. Med. Chem., 1998; 41:1163–1171.
Partial European Search Report for Appl. No. EP 00914419, dated May 2, 2002.
Picciola G.: "Sintesi Di Acidi Chiazolinoici E Benzossazinonici E Studio Delle Loro Proprieta Antiiniammatorie" Farmaco, Edizione Sientifica, IT, Societa Chimica Italiana, Pavia vol 31, No. 9 pp. 655–664 (p. 662 table III) (1976)–.
Leone–Bay et al., J. Med Chem. Vol 39, No. 13 pp. 2571–2578 (1996).
Cynkowska, G. et al., American Chemical Society 215$^{th}$ Meeting, Dallas Texas (1998).

* cited by examiner

Primary Examiner—Thurman K. Page
Assistant Examiner—S. Tran
(74) Attorney, Agent, or Firm—Darby & Darby

(57) ABSTRACT

Polymeric delivery agents, delivery agent compounds and compositions comprising them which are useful in the delivery of active agents are provided. Methods of administration and preparation are provided as well.

27 Claims, No Drawings

POLYMERIC DELIVERY AGENTS AND DELIVERY AGENTS COMPOUNDS

This application is a 371 of International Application No. PCT/US00/0476, filed Jan. 7, 2000, which was published in English as International Publication No. WO 00/40203 and claims benefit of U.S. Provisional Patent Application No. 60/115,273, filed Jan. 8, 1999, the entire disclosure of which is incorporated by reference herein.

FIELD OF THE INVENTION

The present invention relates to compositions for delivering active agents, and particularly biologically or chemically active agents. The compositions comprise a polymeric delivery agent or delivery agent compound which facilitates the delivery of the active agent to a target. These polymeric delivery agents and delivery agent compounds are well suited to form non-covalent mixtures with active agents for administration to animals. Methods for the preparation and for the administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself. Biologically or chemically active agents are particularly vulnerable to such barriers.

In the delivery to animals of pharmacological and therapeutic agents, barriers are imposed by the body. Physical barriers such as the skin and various organ membranes are relatively impermeable to certain active agents but must be traversed before reaching a target, such as the circulatory system. Chemical barriers include, but are not limited to, pH variations in the gastrointestinal (GI) tract and degrading enzymes.

Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rendered ineffective or may be destroyed in the GI tract by acid hydrolysis, enzymes, or the like, or may simply not be absorbed.

Many delivery agents are fairly hydrophobic, whereas many active agents are hydrophilic. The differential aqueous solubility between the delivery agent and the active agent can be problematic in designing commercially acceptable dosage formulations which exhibit biological activity in vivo. Thus, the ability to alter the solubility of a delivery agent would allow one to tailor the delivery agent to meet the needs of the cargo in order to optimize its bioavailability.

The pH within the gastrointestinal tract typically ranges from about 1 to about 8, while many delivery agents remain soluble over a range of only 2–2.5 pH units. During oral delivery, a significant amount of such a delivery agent could precipitate out in the stomach due to the local acidity. The precipitated delivery agent would then be unavailable for delivery of active agent to a point further along the GI tract. Increasing the span of pH solubility of the delivery agent would allow more effective delivery at lower concentrations of delivery agent.

Delivery agents generally tend to self-aggregate into micellular-like structures. The competition between self association and association with the active agent typically results in at least a portion of the delivery agent being unavailable for effective delivery of the active agent. Thus, a corresponding portion of the active agent that was administered may not be effectively delivered to the target. Inhibiting self aggregation of the delivery agent would increase the availability of delivery agent for delivery of the active agent.

Various delivery agents for oral administration of active agents have been developed in recent years. These delivery agents include proteinoids, modified vegetable proteins, acylated or sulfonated amino acids, acylated or sulfonated amino acid ketones, and acylated or sulfonated amino acid aldehydes. See, U.S. Pat. Nos. 5,401,516; 5,443,841; 5,451,410; 5,541,155; 5,629,020; 5,643,957; 5,693,338; 5,709,861; 5,714,167; 5,766,633; 5,773,647; 5,792,451; 5,820,881; 5,863,944; 5,866,536; and RE35,862. These delivery agents promote systemic absorption of active agents in the gastrointestinal tract. The interaction between the delivery agent and the active agent, as well as the interaction between the delivery agent and the cell membrane, may be important for absorption. See, U.S. Pat. No. 5,714,167.

There is a need for delivery agents whose solubility can be modified for a particular need, thereby changing the concentration of soluble delivery agent which is available for delivery of an active agent.

Therefore, there is a need for alternate and improved delivery agents.

SUMMARY OF THE INVENTION

The present invention provides polymeric delivery agents which are useful in the delivery of active agents. The polymeric delivery agent comprises a polymer conjugated to a modified amino acid or derivative thereof via a linkage group selected from the group consisting of —NHC(O)NH—, —C(O)NH—, —NHC(O)—, —OOC—, —COO—, —NHC(O)O—, —OC(O)NH—, —CH$_2$NH—, —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid The modified amino acids may be acylated or sulfonated amino acids, ketones or aldehydes of acylated or sulfonated amino acids, salts thereof, or polyamino acids or polypeptides of any of the foregoing.

The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG) and derivatives thereof, such as PEG-maleic anhydride copolymers; and derivatives and combinations thereof. The molecular weight of the polymer typically ranges from about 100 to abut 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

According to one embodiment, the polymeric delivery agent comprises units having the formula

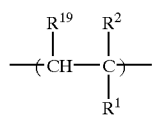

or salts thereof where $R^1$ is a modified amino acid which is bonded to the polymer via a linkage group selected from the group consisting of —NHC(O)NH—, —C(O)NH—, —NHC(O)—, —OOC—, —COO—, —NHC(O)O—, —CC(O)NH—, —CH$_2$NH—, —NHCH$_2$—, —CH$_2$NHC(O)O—, —OC(O)NHCH$_2$—, —CH$_2$NHCOCH$_2$O—, —OCH$_2$(O)NHCH$_2$—, —NHC(O)CH$_2$O—, —OCH$_2$C(O)NH—, —NH—, —O—, and carbon-carbon bond; $R^2$ is H or —CH$_3$; and $R^{19}$ is H or —COCH. Preferably, $R^1$ is —$R^3$—$R^4$ where $R^3$ is —NHC(O)NH—, —C(O)NH—, —NHC(O)—, —OOC—, —COO—, —NHC(O)O—, —OC(O)NH—, —CH$_2$NH—, —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, or carbon-carbon bond; and $R^4$ has the formula

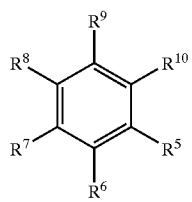

where

R$^5$, R$^6$, R$^7$, R$^8$, and R$^9$ are independently a bond to R$^3$, or H, Cl, Br, F, —OH, —CH$_3$, —CH$_3$, or —(CH$_2$)$_m$CH$_3$;

R$^{10}$ is a bond to R$^3$ or —COOH, or —C(O)NH—R$^{11}$—R$^{12}$;

R$^{11}$ is a substituted or unsubstituted, linear or branched alkylene Slaving a chain length of from about 1 to about 11 or —R$^{13}$—R$^{14}$—;

R$^{12}$ is a bond to R$^3$ or is —COOH, —NH$_2$, —OH, —C(O)—R$^{15}$, —COO—R$^{15}$, —NHR$^{15}$, —OR$^{15}$, Cl, or Br;

R$^{13}$ is a substituted or unsubstituted phenylene;

R$^{14}$ is a substituted or unsubstituted, linear or branched alkylene having a chain length of from about 1 to about 5;

R$^{15}$ is a bond to R$^3$; and m is from about 1 to about 4.

Preferably, R$^4$ is selected from the group consisting of

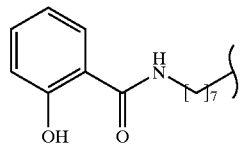

I

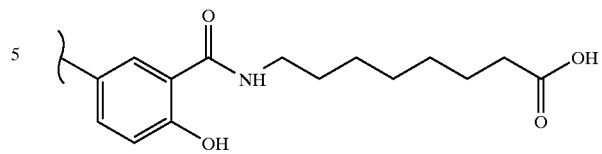

(I-COOH)

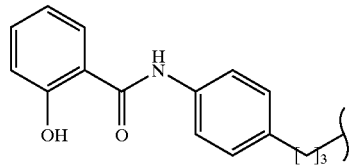

II

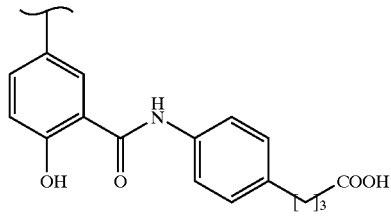

(II-COOH)

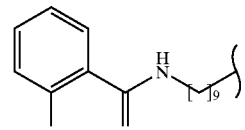

III

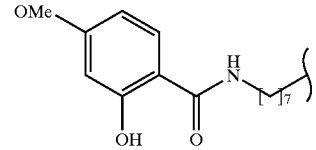

IV

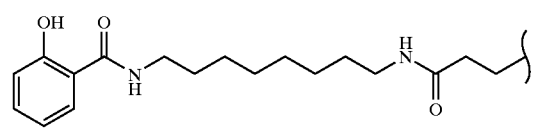

V

VI

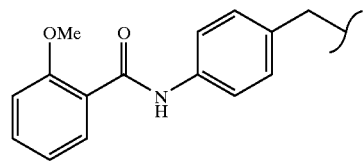

VII

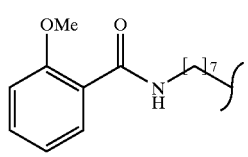

VIII

-continued

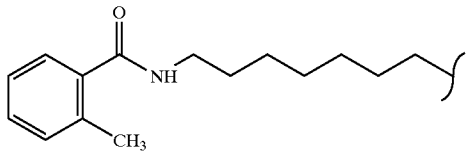
IX

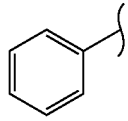
X

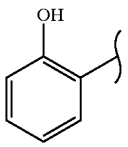
XI and salts thereof.

Preferably, $R^9$ is —$OCH_3$ or —OH. According to a preferred embodiment, $R^{10}$ is —NH—$R^{11}$—$R^{12}$ and $R^{11}$ is —$(CH_2)_7$—, —$(CH_2)_9$—, —$(C_6H_5)$—, —$(CH_2)$—, —$(C_6H_5)$—$CH_2$—, or —$(CH_2)_8$—NH—C(O)—$CH_2$—.

Another embodiment is a polymeric delivery agent having units of the formula $$R^{16}—R^{24}—CH_2CH_2—R^{17}$$

or salts thereof where $R^{16}$ is defined as $R^1$ above; $R^{17}$ is —OH, —$OCH_3$, or —$R^{18}$; $R^{18}$ is defined as $R^1$ above; and $R^{24}$ is a polymer having units of —$(CH_2CH_2O)$—, —$(CH(CH_3)CH_2O)$—, or a combination thereof. $R^{24}$ typically contains from about 3 to about 200 polymeric units. $R^{24}$ may be a random copolymer or a block copolymer. $R^{18}$ may be the same or different than $R^{16}$.

A preferred embodiment of the polymeric delivery agent has units of the formula

or salts thereof where $R^{16}$, $R^{17}$, and $R^{18}$ are defined as above; $R^{23}$ is H or —$CH_3$; and n is from about 3 to about 200. Preferably, $R^{16}$ and $R^{18}$ are —OOC—$R^4$. According to a preferred embodiment, $R^{17}$ is —$OCH_3$. According to another preferred embodiment, $R^{16}$ is —NHC(O)-$R^4$ or —NHC(O)O—$R^4$ and n ranges from about 4 to about 15.

Yet another embodiment is a polymeric delivery agent having units of the formula

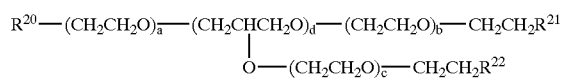

or salts thereof where $R^{20}$, $R^{21}$, and $R^{22}$ independently are H or are defined as $R^1$ above; a, b, and c independently are integers from about 1 to about 50; and d ranges from about 2 to about 10. Preferably, $R^{20}$, $R^{21}$, and $R^{22}$ independently are —COO—$R^4$. Preferably, d is about 6.

Examples of polymeric delivery agents and units for the polymeric delivery agents include, but are not limited to,

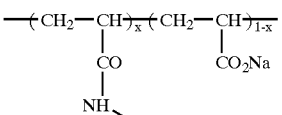
Conjugate 1 wherein x is 0.02 to 0.5, preferably 0.05 (Conjugate 1 is a random polymer);

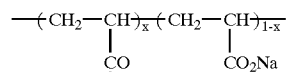
Conjugate 2

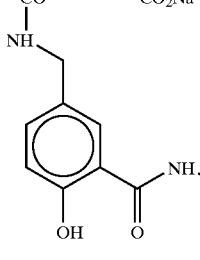

wherein x is 0.02 to 0.5, preferably 0.06 (Conjugate 1 is a random polymer);

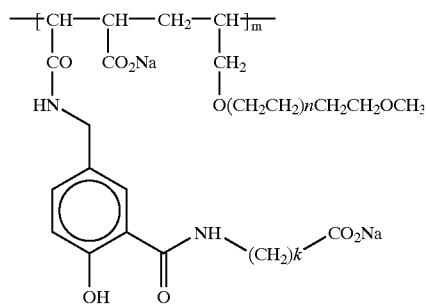

wherein
k=1–11, preferably 7 or 9
n=10 to 50, preferably 33, and
m=5 to 15, preferably 9.
Conjugate 3 is the rove structure where k=7, n=33 and m=8;
I-COO—$CH_2CH_2O(CH_2CH_2O)_5CH_2CH_2OH$ Conjugate 4.
I-COO—$CH_2CH_2O(CH_2CH_2O)_3CH_2CH_2OH$ Conjugate 5
I-COO—$CH_2CH_2O(CH_2CH_2O)_5CH_2CH_2OCH_3$ Conjugate 6
I-COO—$CH_2CH_2O(CH_2CH_2O)_7CH_2CH_2OH$ Conjugate 7
II-COO—$CH_2CH_2O(CH_2CH_2O)_5CH_2CH_2OH$ Conjugate 8
III-COO—$CH_2CH_2O(CH_2CH_2O)_7CH_2CH_2OH$ Conjugate 9

I-COO—CH$_2$CH$_2$O(CH$_2$CH$_2$O)$_{11}$CH$_2$CH$_2$OH Conjugate 10

I-COO—CH$_2$CH$_2$O(CH$_2$CH$_2$O)$_{102}$CH$_2$CH$_2$OOC-I Conjugate 11

PEG branched (8 arms):

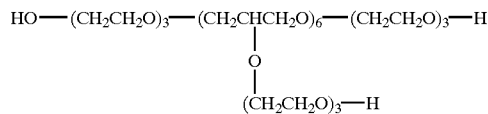

The modified amino acid I-COO is attached at the —OH group through an ester linkage at 4 of the 8 "arms". Conjugate 12

VIII-COO—CH$_2$CH$_2$O(CH$_2$CH$_2$O)$_6$CH$_2$CH$_2$OH Conjugate 27

III-COO—CH$_2$CH$_2$O(CH$_2$CH$_2$O)$_4$CH$_2$CH$_2$OH Conjugate 28

III-COO—CH$_2$CH$_2$O(CH$_2$CH$_2$O)$_6$CH$_2$CH$_2$OH Conjugate 29

PEG branched (8 arms):

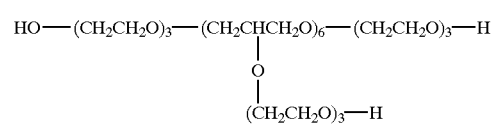

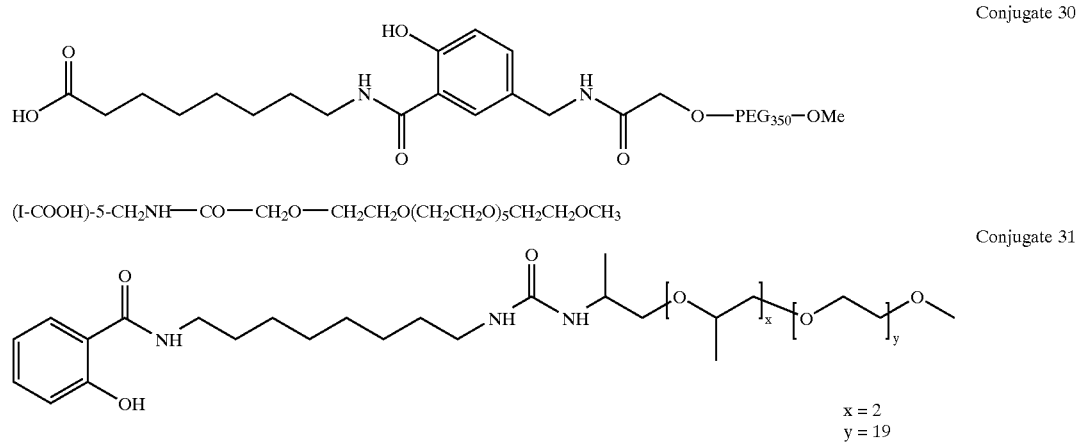

Conjugate 30

(I-COOH)-5-CH$_2$NH—CO—CH$_2$O—CH$_2$CH$_2$O(CH$_2$CH$_2$O)$_5$CH$_2$CH$_2$OCH$_3$

Conjugate 31 x = 2
y = 19

I-COO—CH$_2$CH$_2$O(CH$_2$CH$_2$O)$_{14}$CH$_2$CH$_2$OCH$_3$ Conjugate 13

IV-COO—CH$_2$CH$_2$O(CH$_2$CH$_2$O)$_4$CH$_2$CH$_2$OH Conjugate 14

V-COO—CH$_2$CH$_2$O(CH$_2$CH$_2$O)$_4$CH$_2$CH$_2$OH Conjugate 15

IV-COO—CH$_2$CH$_2$O(CH$_2$CH$_2$O)$_6$CH$_2$CH$_2$OH Conjugate 16

I-CH$_2$NH—CO—O—CH$_2$CH$_2$O(CH$_2$CH$_2$O)$_5$CH$_2$CH$_2$OCH$_3$ Conjugate 17

I-CH$_2$NH—CH$_2$CH$_2$O(CH$_2$CH$_2$O)$_5$CH$_2$CH$_2$OCH$_3$ Conjugate 18

II-COO—CH$_2$CH$_2$O(CH$_2$CH$_2$O)$_{10}$CH$_2$CH$_2$OCH$_3$ Conjugate 19

II-COO—CH$_2$CH$_2$O(CH$_2$CH$_2$O)$_5$CH$_2$CH$_2$OCH$_3$ Conjugate 20

I-COO—CH$_2$CH$_2$O(CH$_2$CH$_2$O)$_{10}$CH$_2$CH$_2$OCH$_3$ Conjugate 21

I-CH$_2$NH—CO—CH$_2$O—CH$_2$CH$_2$O(CH$_2$CH$_2$O)$_5$CH$_2$CH$_2$OCH$_3$ Conjugate 22

I-CH$_2$NH—CO—CH$_2$O—CH$_2$CH$_2$O(CH$_2$CH$_2$O)$_{10}$CH$_2$CH$_2$OCH$_3$ Conjugate 23

VI-COO—CH$_2$CH$_2$O(CH$_2$CH$_2$O)$_5$CH$_2$CH$_2$OCH$_3$ Conjugate 24

VI-COO—CH$_2$CH$_2$O(CH$_2$CH$_2$O)$_{10}$CH$_2$CH$_2$OCH$_3$ Conjugate 25

VII-COO—CH$_2$CH$_2$O(CH$_2$CH$_2$O)$_{10}$CH$_2$CH$_2$OCH$_3$ Conjugate 26

The modified amino acid I-COO is attached at the —OH group through an ester linkage at 6 of the 8 "arms". Conjugate 32

I-COO—CH$_2$CH$_2$O—(CH$_2$CH$_2$O)$_{11}$—CH$_2$CH$_2$OOC-I Conjugate 33

(I-COOH)-5—CH$_2$NH—CO—OCH$_2$CH$_2$—(OCH$_2$CH$_2$)$_{43}$—OCH$_2$CH$_2$—OCH$_3$ Conjugate 34

PEG branched (8 arms):

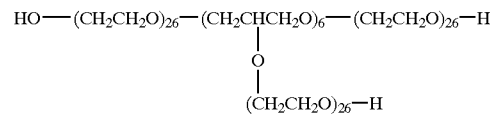

The modified amino acid I-COO is attached at the —OH group through an ester linkage at 4 of the 8 "arms". Conjugate 35

The modified amino acid I-COO is attached at the —OH group through an ester linkage at 5 of the 8 "arms". Conjugate 36

The modified amino acid I-COO is attached at the —OH group through an ester linkage at 7 of the 8 "arms". Conjugate 37

The modified amino acid I-COO is attached at the —OH group through an ester linkage at 8 of the 8 "arms". Conjugate 38

I-COO—CH$_2$CH$_2$O—(CH$_2$CH$_2$O)$_{45}$—CH$_2$CH$_2$OOC-I Conjugate 39

I-NH—COO—CH$_2$CH$_2$O—(CH$_2$CH$_2$O)$_{42}$—CH$_2$CH$_2$OCH$_3$ Conjugate 40

I-COO—CH$_2$CH$_2$O—(CH$_2$CH$_2$O)$_4$—CH$_2$CH$_2$OOC-I Conjugate 41

XI-COO—CH$_2$CH$_2$O—(CH$_2$CH$_2$O)$_4$—CH$_2$CH$_2$OH Conjugate 42

X-COO—CH$_2$CH$_2$O—(CH$_2$CH$_2$O)$_{10}$—CH$_2$CH$_2$OCH$_3$ Conjugate 43

X-COO—CH$_2$CH$_2$O—(CH$_2$CH$_2$O)$_{11}$—CH$_2$CH$_2$OH Conjugate 44

X-COO—CH$_2$CH$_2$O—(CH$_2$CH$_2$O)$_{20}$—CH$_2$CH$_2$O—CO-X conjugate 45

X-COO—CH$_2$CH$_2$O—(CH$_2$CH$_2$O)$_{20}$—CH$_2$CH$_2$OH Conjugate 46

X-COO—CH$_2$CH$_2$O—(CH$_2$CH$_2$O)$_{11}$—CH$_2$CH$_2$O—CO-X Conjugate 47

IX-COO—CH$_2$CH$_2$O—(CH$_2$CH$_2$O)$_5$—CH$_2$CH$_2$OCH$_3$ Conjugate 48

The number of polymeric units specified in the aforementioned polymeric delivery are an average number of units. The number of units in the polymers typically may vary by up to about 10%.

Another embodiment provides a composition comprising (A) at least one active agent; and (B) at least one of the aforementioned polymeric delivery agents. The active agent preferably is a biologically or chemically active agent. Methods for the preparation and administration of the composition are also provided. These compositions are useful in the delivery of active agents to selected biological systems and for increasing or improving the bioavailability of the active agent compared to administration of the active agent without the delivery agent.

The invention also includes a method of preparing a polymeric delivery agent by conjugating a modified amino acid to a polymer, via one of the aforementioned linkage groups.

The invention further includes delivery agent compounds having the formulae

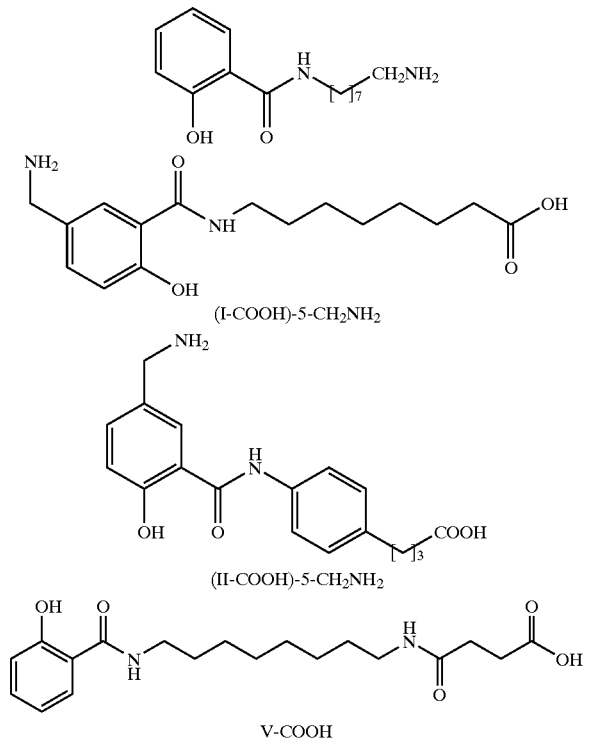

and salts thereof, including but not limited to sodium salts. These delivery agent compounds are useful for facilitating the delivery of an active agent. Another embodiment is a composition comprising one of the aforementioned delivery agent compounds and an active agent.

DETAILED DESCRIPTION OF THE INVENTION

These compositions may be used to deliver various active agents through or across various biological, chemical, and physical barriers and are particularly suited for delivering active agents that are subject to environmental degradation. The compositions of the subject invention are particularly useful for delivering or administering biologically or chemically active agents to any animals, including but not limited to birds such as chickens; mammals, such as rodents, cows, pigs, dogs, cats, primates, and particularly humans; and insects.

Other advantages of the present invention include the use of easy-to-prepare, inexpensive raw materials. The compositions and the methods of the present invention are cost effective, easy to perform, and amenable to industrial scale up for commercial production.

The presently disclosed compositions deliver active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems as well as traversing the blood-brain barrier. Coadministration of an active agent and a polymer-delivery agent conjugate results in an increased bioavailability of the active agent compared to administration of the active agent alone.

The term "salts" as used in this application includes but are not limited to organic and inorganic salts, for example alkali-metal salts, such as sodium, potassium and lithium; alkaline-earth metal salts, such as magnesium, calcium or barium; ammonium salts; basic amino acids such as lysine or arginine; and organic amines, such as dimethylamine or pyridine. Preferably, the salts are sodium salts.

Active Agents

Active agents suitable for use in the present invention include biologically active agents, and chemically active agents, including, but not limited to, pesticides, pharmacological agents, and therapeutic agents.

For example, biologically active agents suitable for use in the present invention include, but are not limited to, proteins, polypeptides; peptides; hormones; polysaccharides, and particularly muco-polysaccharides and mixtures thereof; carbohydrates; lipids; other organic compounds; and particularly compounds which by themselves do not pass (or which pass only a fraction of the administered dose) through the gastrointestinal mucosa and/or are susceptible to chemical and/or enzymatic cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormone (rhGH), bovine growth hormones, and porcine growth hormones; growth hormone-releasing hormones; interferons, including α, β and γ; interleukin-1; interleukin-2; insulin, including porcine, bovine, human and human recombinant, optionally having counter ions including sodium, zinc, calcium and ammonium; insulin-like growth factor, including IGF-1; heparin, including unfractionated heparin, heparinoids, dermatans, chondroitins, low molecular weight heparin, very low molecular weight heparin and ultra low molecular weight haparin; calcitonin, including salmon, eel and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferroxamine (DFO); parathyroid hormone (PTH), including its fragments; antimicrobials, including anti-fungal agents; vitamins; analogs, fragments, mimetics or polyethylene glycol (PEG)-modified derivatives of these compounds; or any combination thereof.

Modified Amino Acids

The modified amino acid may be an N-acylated or sulfonated amino acid, a ketone or aldehyde of an acylated or sulfonated amino acid, salts thereof, and a polyamino acid or polypeptide which includes any of the foregoing.

N-acylated and sulfonated amino acids, poly amino acids, and peptides include, but are not limited to, amino acids which have been N-acylated or sulfonated, and poly amino acids and peptides in which at least one amino acid has been modified, by acylating or sulfonating at least one free amine group with an acylating or sulfonating agent which reacts with at least one of the free amine groups present.

Preferably, the modified amino acids comprise one of the following structures:

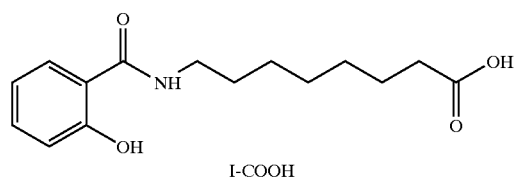

I-COOH

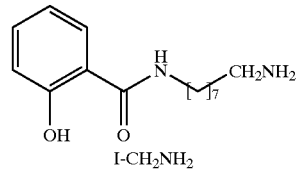

I-CH₂NH₂

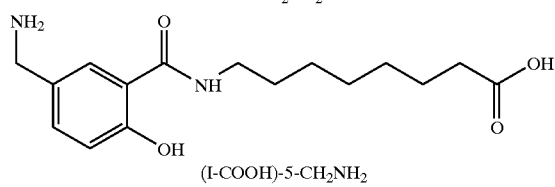

(I-COOH)-5-CH₂NH₂

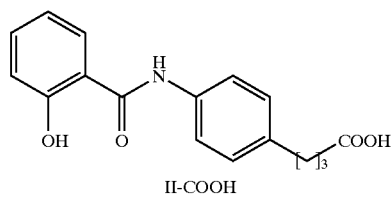

II-COOH

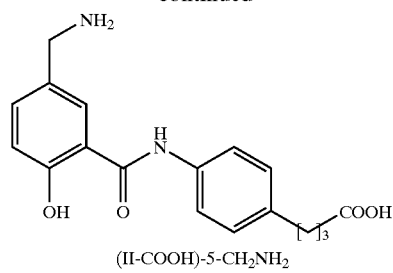

(II-COOH)-5-CH₂NH₂

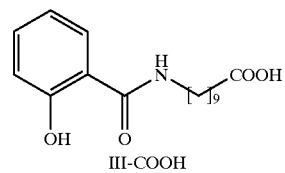

III-COOH

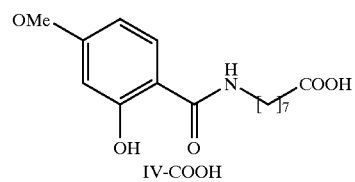

IV-COOH

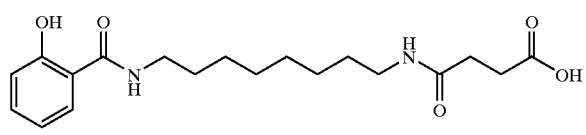

V-COOH

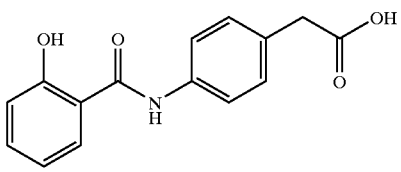

VI-COOH

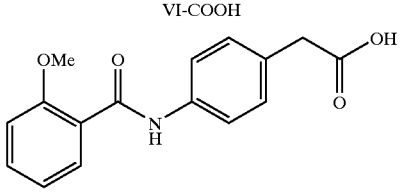

VII-COOH

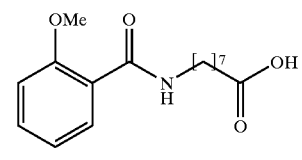

VIII-COOH

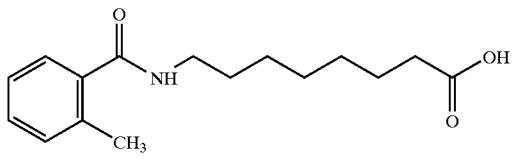

IX-COOH

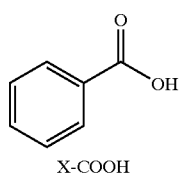

X-COOH

-continued

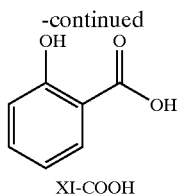

XI-COOH and salts thereof, including but not limited to sodium salts.

The modified amino acids may be in the form of salts. Salts include but are not limited to organic and inorganic salts, for example alkali-metal salts, such as sodium, potassium and lithium; alkaline-earth metal salts, such as magnesium, calcium or barium; ammonium salts; basic amino acids such as lysine or arginine; and organic amines, such as dimethylamine or pyridine. Preferably, the salts are sodium salts.

An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked, e.g. an ester, anhydride, or an anhydride linkage. Peptides can vary in length from dipeptides with two amino acids to poly peptides with several hundred amino acids. One or more of the amino acid or peptide units may be acylated or sulfonated.

N-acylated or sulfonated amino acids are typically prepared by modifying the amino acid or an ester thereof Many of these compounds are prepared by acylation or sulfonation with agents having the formula

X-Y-R wherein:
  R is the appropriate radical to yield the modification indicated in the final product,
  Y is C=O or $SO_2$, and
  X is a leaving group.

Typical leaving groups include, but are not limited to, halogens such as, for example, chlorine, bromine, and iodine. Additionally, the corresponding anhydrides are modifying agents.

N-acylated or sulfonated amino acids can be readily prepared from amino acids by methods within the skill of those in the art based upon the present disclosure. For example, N-acylated or sulfonated amino acids may be derived from aminobutyric acid, aminocaproic acid, and aminocaprylic acid. Further, the N-acylated or sulfonated amino acid above may be prepared by reacting the single amino acid with the appropriate modifying agent which reacts with a free amino moiety present in the amino acids to form amides. Protecting groups may be used to avoid unwanted side reactions as would be known to those skilled in the art.

The amino acid can be dissolved in aqueous alkaline solution of a metal hydroxide, e.g., sodium or potassium hydroxide, and heated at a temperature ranging between about 5° C. and about 70° C., preferably between about 10° C. and about 40° C., for a period ranging between about 2 hour and about 4 hours, preferably about 2.5 hours. The amount of alkali employed per equivalent of $NH_2$ groups in the amino acid generally ranges between about 1.25 and about 3 mmole, preferably between about 1.5 and about 2.25 mmole per equivalent of $NH_2$. The pH of the solution generally ranges between about 8 and about 13, preferably ranging between about 10 and about 12.

Thereafter, the appropriate amino modifying agent is added to the amino acid solution while stirring. The temperature of the mixture is maintained at a temperature generally ranging between about 5° C. and about 70° C., preferably between about 10° C. and about 40° C., for a period ranging between about 1 and about 4 hours. The amount of amino modifying agent employed in relation to the quantity of amino acid is based on the moles of total free $NH_2$ in the amino acid. In general, the amino modifying agent is employed in an amount ranging between about 0.5 and about 2.5 mole equivalents, preferably between about 0.75 and about 1.25 equivalents, per molar equivalent of total $NH_2$ group in the amino acid.

The reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded, and the N-acylated or sulfonated amino acid is collected from the lower layer by filtration or decantation. The crude N-acylated or sulfonated amino acid is then dissolved in water at a pH ranging between about 9 and about 13, preferably between about 11 and about 13. Insoluble materials are removed by filtration and the filtrate is dried in vacuo The yield of N-acylated or sulfonated amino acid generally ranges between about 30 and about 60%, and usually about 45%.

If desired, amino acid esters, such as, for example benzyl, methyl, or ethyl esters of amino acid compounds, may be used to prepare the N-acylated or sulfonated amino acids of the invention. The amino acid ester, dissolved in a suitable organic solvent such as dimethylformamide, pyridine, or tetrahydrofuran is reacted with the appropriate amino modifying agent at a temperature ranging between about 5° C. and about 70° C., preferably about 25° C., for a period ranging between about 7 and about 24 hours. The amount of amino modifying agent used relative to the amino acid ester is the same as described above for amino acids. This reaction may be carried out with or without a base such as, for example, triethylamine or diisopropylethylamine.

Thereafter, the reaction solvent is removed under negative pressure and the ester functionality is removed by hydrolyzing the N-acylated or sulfonated amino acid ester with a suitable alkaline solution, e.g. 1N sodium hydroxide, at a temperature ranging between about 50° C. and about 80° C., preferably about 70° C., for a period of time sufficient to hydrolyze off the ester group and form the N-acylated or sulfonated amino acid having a free carboxyl group. The hydrolysis mixture is then cooled to room temperature and acidified, e.g. aqueous 25% hydrochloric acid solution, to a pH ranging between about 2 and about 2.5. The N-acylated or sulfonated amino acid precipitates out of solution and is recovered by conventional means such as filtration or decantation. Benzyl esters may be removed by hydrogenation in an organic solvent using a transition metal catalyst.

The N-acylated or sulfonated amino acid may be purified by recrystallization or by fractionation on solid column supports Suitable recrystallization solvent systems include acetonitrile, methanol and tetrahydrofuran. Fractionation may be performed on suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0–500 mm sodium chloride gradient is employed.

Polymers

The polymers of the present invention may be natural or synthetic and comprise two or more monomers. The monomers may be the same or different, and the polymer may be linear or non-linear Polymers include but are not limited to branched or cyclic polymers. The polymers may be copolymers including two or more different monomers, or homopolymers including a single-type of monomeric repeat. Further, polymers may be random or alternating, directed, bifunctional, polyfunctional, cross-linked, regular lattice, intermittent lattice, or amorphous.

The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG) and derivatives thereof, such as PEG-maleic anhydride copolymers; and derivatives and combinations thereof. The molecular weight of the polymer typically ranges from about 100 to about 200,000 daltons The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Polymers may be in the form of one or more salts. Salts include but are not limited to organic and inorganic salts, for example alkali-metal salts, such as sodium, potassium and lithium; alkaline-earth metal salts, such as magnesium, calcium or barium; ammonium salts; basic amino acids such as lysine or arginine; and organic amines, such as dimethylamine or pyridine. Preferably, the salts are sodium salts.

Polymeric Delivery Agent (Conjugates)

One or more of the modified amino acids may be conjugated (covalently attached) to one or more of the monomeric units of the polymer via one of the aforementioned linkage groups.

Many of the polymeric delivery agents have solubility greater than about 200 mg/mL, and have greater solubility than the corresponding modified amino acids alone. However, like most poloxamers, the solubility of PEG conjugates decreases at higher temperatures and can be characterized by the cloud point or lower critical solution temperature (LCST). The LCST is dependent on the ratio of hydrophilic/hydiophobic units in the conjugate and can be changed easily.

In general, the polymeric delivery agents of the present invention may be prepared as follows. For vinyl polymeric delivery agents, such as PAA and PAA/MA polymers, the polymer and modified amino acids may each be separately dissolved in an appropriate solvent, e.g., dimethyl formamide (DMF), to yield solutions A and B, respectively. Solution B is warmed to about 60–70° C., in the presence of a base, e.g. triethylamine. Solution B is then added to solution A and the mixture is stirred at room temperature for 24 hours. The polymeric delivery agents precipitates with the addition of dilute acid or base and is collected by centrifugation. The polymeric delivery agents is then hydrolyzed, dialyzed against water, and lyophilized.

The resultant polymeric delivery agents may be analyzed by Size Exclusion Chromatography (SEC) in order to determine the approximate molecular weight of the polymer and the nitrogen content of the conjugate may be used to approximate the amount of modified amino acid bound to the polymer in the polymeric delivery agent. Preferably, there is between about 5 and 15% w/w bound modified amino acid in the polymeric delivery agent, and more preferably, there is between about 10 and 15% w/w bound modified amino acid unit in the polymeric delivery agent.

For PEG delivery agents with ester linkages, a carboxyl-containing deliver agent reacts with PEG or PEG methyl ether in toluene at 150–160° C. in the presence of p-toluene sulfonic acid as a catalyst for 3–4 hours. Water generated by the reaction is removed with a Dean-Stark trap. Reverse phase HPLC is used to monitor the reaction. The reaction mixture is washed with saturated $NaHCO_3$ water solution to remove unreacted starting materials and the catalyst. The polymeric delivery agents are obtained after evaporation of toluene. The structure is further confirmed by nitrogen analysis and $^1H$ NMR.

PEG delivery agents with amide, amino or urethane linkages may be prepared by reaction of an amino-containing modified amino acids with an appropriately activated polyethylene glycol in pyridine at 70–80° C. for 4–5 hours and at room temperature for about 24 hours. Pyridine is then removed by evaporation under reduced pressure. The residue is then dissolved in an organic solvent, e.g., methylene chloride, and the solution is washed with dilute HCl aq., NaCl aq., and $NaHCO_3$ aq. respectively to remove impurities. Reverse phase RPLC is used to monitor both the reaction and the work-up process. The polymeric delivery agents is obtained after evaporation of the organic solvent. The structure is further confirmed by nitrogen analysis and $^1H$ NMR.

In order to prepare PEG delivery agents with urea linkages, a two step process was used. First, a urethane derivative based on the reaction of an amino terminated hydrophobic compound and 4-nitrophenyl chloroformate is prepared. The reaction is very fast and carried out at room temperature in pyridine solution. The intermediate urethane derivative contains a good leaving group that can be eliminated on attack of nucleophilic agents. When this intermediate is reacted with an amino-terminated PEG, both 4-nitrophenol and the PEG adduct with urea linkage were formed.

Delivery Systems

The compositions of the present invention may include one or more active agents. In one embodiment, the polymeric delivery agents or delivery agent compounds of the present invention (collectively "delivery agents") may be used directly as a delivery agent by simply mixing one or more delivery agent with the active agent prior to administration. The administration mixtures may be prepared by mixing an aqueous solution of the delivery agent with an aqueous solution of the active ingredient, just prior to administration.

Alternatively, the delivery agent and the active agent can be admixed during the manufacturing process. The solutions may optionally contain additives such as phosphate buffer salts, citric acid, acetic acid, gelatin, and gum acacia.

Stabilizing additives may be incorporated into the delivery agent solution. With some active agents, the presence of such additives promotes the stability and dispersibility of the agent in solution. The stabilizing additives may be employed at a concentration ranging between about 0.1 and 5% (w/v), preferably about 0.5% (w/v). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The amount of active agent is an amount effective to accomplish the purpose of the particular active agent. The amount in the composition typically is a pharmacologically or biologically effective amount. However, the amount can be less than a pharmacologically or biologically effective amount when the composition is used in a dosage unit form, such as a solid, such as a capsule, a tablet, or a powder, or a liquid, because the dosage unit form may contain a multiplicity of delivery agent or active agent compositions or may contain a divided pharmacologically or biologically effective amount. The total effective amounts can then be administered in cumulative units containing, in total, pharmacologically or biologically or chemically active amounts of biologically or pharmacologically active agent.

The total amount of active agent to be used can be determined by those skilled in the art. However, because the presently disclosed delivery agents provide efficient delivery, lower amounts of biologically or chemically active agent than chose used in prior dosage unit forms or delivery systems may be administered to the subject, while still achieving the same blood levels and therapeutic effects.

The amount of delivery agents in the present composition is a delivery effective amount and can be determined for any particular deliver agents or active agent by methods known to those skilled in the art. It will be this amount effective for delivery of the active agent by the chosen route of delivery.

Dosage unit forms can also include any of excipients; diluents; disintegrants; lubricants; plasticizers; colorants; and dosing vehicles, including, but not limited to water, 1,2-propane diol, ethanol, olive oil, or any combination thereof.

Administration of the present compositions or dosage unit forms preferably is oral, intracolonic or intraduodenal. Particularly, the compositions of the present invention are useful in orally administering active agents, especially those that are not ordinarily orally deliverable.

The delivery compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The compositions of the subject invention are useful for administering biologically or chemically active agents to animals. The system is particularly advantageous for delivering biologically or chemically active agents which would otherwise be destroyed or rendered less effective by conditions encountered before the active agent has reached its target zone (i.e. the area in which the active agent of the delivery composition are to be released) and within the body of the animal to which they are administered.

DESCRIPTION OF THE PREFERRED EMBODIMENTS

The following examples illustrate the invention without limitation. All parts are given by weight unless otherwise indicated. The number of polymeric units and molecular weights of the polymers specified in the examples are an average number of units and average molecular weights. The number of units and molecular weights in the polymers typically varies by up to about 10%.

EXAMPLE 1a

Preparation of 8-N(2-Hydroxy-5-aminomethylbenzoyl) Aminocaprylic Acid ((I-COOH)-5-$CH_2NH_2$), Hydrogen Chloride Salt 8-N(2-methoxybenzoyl)aminocaprylic acid (7.5 g, 25.6 mmol, 1 equiv.) was mixed with formaldehyde (30.7 ml, 410 mmol, 16 equiv.) and hydrochloric acid (62.6 ml, 37%, 644 mmol, 25 equiv.). The mixture was stirred and bubbled under HCl gas at room temperature for 3 hours. Crude 8-N(2-methoxy-5-chloromethylbenzoyl)aminocaprylic acid (compound 1) was obtained by removal of formaldehyde and HCl. Pure compound 1 was obtained by recrystallization in acetonitrile (4.5 g, 51.4%).

The purified 8-N(2-methoxy-5-chloromethylbenzoyl) aminocaprylic acid (4.5 g, 13.2 mmol, 1 equiv.) and hexamethylenetetrarcine (1.85 g, 13.2 mmol, 1 equiv.) were refluxed in chloroform for 1 hour. The chloroform was evaporated. The residue was refluxed in a mixed solution of methyl alcohol (30 ml) and HCl (10 ml, 37%) for 2 hours. 8-N(2-methoxy5-aminomethylbenzoyl)aminocaprylic acid (compound 2) was obtained by removal of the mixed solvent (3.6 g, 76.6%). Compound 2 (3.5 g, 9.75 mmol, 1 equiv.) was dissolved in dichloromethane (50 ml). Boron tribromide (1.184 ml, 19.5 mmol, 2 equiv.) was added to the reaction mixture at 0° C. and stirred for 2 hours. The product was filtered and the residue was washed with dichloromethane (20 ml×2). 8-N(2-Hydroxy 5-aminomethylbenzoyl) aminocaprylic acid, hydrochloride salt was obtained as white solid (1.8 g, 47.37%). Properties are listed below:

H NMR (300 Mhz, DMSO-$d^6$) δ: 1.29 (6H, br s). 1.5 (4H, m) 2.18 (2H, t, J 7.3 Hz). 3.30 (2H, q, J 6.17 Hz). 3.94 (2H, q, J 6.56 Hz). 6.97 (1H, d, J 8.7 Hz) 7.49 (1H, d, J 6.3 Hz). 8.0 (1H, s). 8.12 (3H, br s) 12.0 (1H, s). 12.5 (1H, s). Anal. for $C_{16}H_{25}N_2O_4Cl$: Calculated: C: 55.73; H: 7 26; N: 8.12; Cl: 10.30. Found: C: 55.59; H: 7.38; N: 8.01; Cl: 10.18.

EXAMPLE 1b

Synthesis of N-(5-Aminomethylsalicyloyl)-4-(4-aminophenyl) Butyric Acid ((II-COOH)-5-$CH_2NH_2$)

Salicylic acid (50 g) was suspended in 120 g of Formalin solution (37%). Hydrogen chloride gas was bubbled through the mixture at 0° C. with mechanical stirring., $ZnCl_2$(10 g) was added as the catalyst 5 minutes later. The hydrogen chloride gas was slowly bubbled through the mixture for 2 hours ("h" or "hr") at 0–15° C. and then for another 3 h at room temperature with stirring. The reaction mixture was refrigerated overnight. The precipitate formed was collected by filtration and dried in air. The crude product (75 g, m.p. 115 130° C.) was recrystallized from benzene to give pure product 5-chloromethylsalic acid (28.5 g, 42%), m.p. 144–147° C.

To a solution of acetic anhydride (1.4 g) and glacial acetic acid (1.7 g), 5 chloromethylsalicylic acid (1.9 g) and one drop (using a pipet) of concentrated sulfuric acid was added with stirring. The reaction mixture was heated slowly to 65–70° C. and held for 1 h. After cooling to room temperature, the reaction mixture was added gradually to 50 ml of ice water. Two hours later, the precipitate formed was collected by filtration and dried In vacuo. Recrystallization from benzene gave the product O-acetyl-5-chloromethylsalicylic acid (1.7 g, 75%), m.p. 119–121° C.

O-Acetyl-5-chloromethylsalicylic acid (2.9 g, 12.7 mmol) and thionyl chloride (15 g, 126 mmol) were added to 30 ml of benzene. The mixture was refluxed for 2 h with stirring. Evaporation of the benzene with excess thionyl chloride gave a syrupy residue to which 30 ml of benzene was added and the solvent evaporated again. The residue was dried in vacuo overnight to remove residual $SOCl_2$ from product O-Acetyl-5-chloromethylsalicyloyl chloride.

4-(4-Aminophenyl)butyric acid (5 g) was dissolved in 40 ml methanol. The solution was refluxed at 80–90° C. with stirring for 4 h while hydrogen chloride gas was bubbled through the solution. After the reaction mixture was cooled to room temperature, ethyl ether (100 ml.) was added. The mixture, which separated into two layers, was refrigerated overnight. The crystalline product was collected by filtration and dried thoroughly. The filtrate was evaporated to dryness and the residue was recrystallized from MeOH/benzene. The total amount of the product methyl 4-(4-aminophenyl)butyrate hydrogen chloride obtained was 5.6 g (87.5%), m.p. 143–145° C.

Methyl 4-(4-aminophenyl)butyrate hydrogen chloride (2.6 g, 11.3 mmol) and triethylamine (2.3 g, 22.6 mmol) were added to 20 ml of methylene chloride (Solution A). O-Acetyl-5-chloromethylsalicyloyl chloride (2.8 g, 11.3 mmol) was dissolved in 20 ml. of methylene chloride (Solution B). The solution A was added dropwise to solution B at 0° C. with stirring. The mixture was stirred at room temperature for another 2 h after the addition. The reaction mixture was then washed with 0.1 N HCl aqueous solution twice (50 ml×2) and saturated NaCl aqueous solution twice (50 ml×2). The organic layer was separated and dried over anhydrous sodium sulfate. The solvent was evaporated under reduced pressure to give a syrupy product [N-O-acetyl-5-chloromethylsalicyloyl)]-4-4(4-aminophenyl) butyric acid methyl ester which was used in the next step without further purification.

The syrupy product obtained above was dissolved in 20 ml of chloroform (Solution C). Hexamethylenetetramine (1.58 g, 11.3 mmol) was dissolved in 20 ml of warm (about 30° C.) chloroform (Solution D). Solution D was added to Solution C and the reaction mixture was refluxed for 2 h at 60–80° C. with stirring. The reaction mixture was then allowed to stand at room temperature overnight. Evaporation of the solvent gave a syrup of the complex of the previous product with hexamethylenetetramine, which solidified after drying in vacuo for several hours.

The solid complex obtained above was dissolved in 5 ml of MeOH. To this solution, 5 ml of concentrated HCl solution was added. The reaction mixture was stirred at 40–50° C. for 4 h. The reaction mixture was then refrigerated overnight. The precipitate ($NH_4Cl$) was filtered off. To the filtrate, 50 ml of MeOH was added. The solvents were evaporated under reduced pressure to give a syrupy product [N-(O-acetyl-5-aminomethylsalicyloyl)]-4-(4-aminophenyl)butyric acid methyl ester hydrogen chloride which was used in the next deprotection step directly without further purification.

The above syrup was dissolved in S ml of MeOH. To this solution, 15 ml of 2N NaOH was added. The milk-like solution was stirred at room temperature for 4 h, while the pH was kept at 10 to 12 by adding NaOH solution. The clear solution was acidified to pH 5 to precipitate the product, which was then collected by filtration, washed with water and ethanol and dried in air. The crude product (3.0 g) was obtained with about 80!% purity checked by $^1$H NMR. The crude product was refluxed in 30 ml of 95% alcohol for 10 min. and then filtered. The insoluble substance was dissolved in 20 ml of water at pH 10 to 11. The solution was then acidified to pH 5. The precipitated product was collected by filtration and dried thoroughly; yield 2.4 g [N-(5-aminomethylsalicyloyl)-]4-(4-aminophenyl)butyric acid ((II-COOH)-5-$CH_2NH_2$) (58% for the last five steps). The m.p. was higher than 240° C. $^1$H NMR (300MHz, DMSO-$d_6$)δppm: 1.75(2H, t), 2.2(2H, t), 2.55(2R, t), 3.95(2H, s)), 7.05(1H, s), 7.15(1H, s), 7.5(1H, d), 7.65(1H, d), 8.18(1H, s), 8.35(1H, br.s).

EXAMPLE 2

Synthesis of I-COOH to XI-COOH

Compound I-COOH may be Prepared as Follows:

A 3 L three-neck round bottom flask:was fitted with an overhead mechanical stirrer and a thermometer, and the flask was cooled in an ice-bath. A solution of 8-aminocaprylic acid (100.0 g, 0.65 moles) in 2 M aqueous sodium hydroxide (1.4L) was charged into the round bottom flask.: The temperature of the solution was kept at about 5° C. and O-acetylsalicyloyl chloride (198.6 g, 0.76 moles, 1.2 equiv.) was added portionwise over 7 hours. The mixture was stirred at 5° C. for 12 hours to yield a yellow homogenous solution. The solution was acidified with 1 M hydrochloric acid to pH 6.8 and was extracted with ethyl acetate (2×600 mL). The pH of the aqueous layer was readjusted to 6.3 and was further extracted with ethyl acetate (2×600 mL). The organic layers were combined, dried over anhydrous sodium sulfate, filtered, and evaporated under reduced pressure. The residue was redissolved in a minimum volume of 2 M aqueous sodium hydroxide, and the pH of the solution was between 9.5 and 10. The mixture was acidified with stirring with 1 M hydrochloric acid to pH of about 6.2, and a solid was formed. The solid was filtered, washed with water (3×300 mL), and recrystallized from 55% methanol/water (v/v) to yield Compound I-COOH as an off-white solid (99.7 g, 57%). Mp 116–117° C. $^1$H NMR (300 M1z, DMSO-$d_6$), δ: 12.70 (1H, br s), 11.95 (1H, br s) 8.81 (1H, t), 7.82 (1H, m), 7.38 (1H, m), 6.84 (2H, m), 2.36 (2H, q), 2.18 (2H, t), 1.50 (4H, br m), 1.28 (6H, m), Anal. Calcd for $C_{15}H_{21}NO_4$; C, 64.50; H, 7.58; 1 N, 5.02. Found: C, 64.26; H, 7.81; N, 4.93.

Compound III-OOH may also be prepared by this same method using 10-amino-caprylic acid available from Tyger Scientific, Inc. (Monmouth Junction, N.J.).

Compounds VIII-COOH and IX-COOH may also be prepared by the same method for preparing Compound I-COOH using the appropriate starting materials.

Compound II-COOH may be Prepared as Follows.

Acetylsalicyloyl chloride (47.00 g, 0.24 mol, 1 equiv.) was added portionwise to a mixture of 4-(4-aminophenyl) butyric acid (50.00 g, 0.28 mol, 1.2 equiv.) in aqueous sodium hydroxide (2M, 300 mL). The reaction was stirred at 25° C. for 2 hours, and the resultant solution was acidified with aqueous hydrochloric acid (1M to pH 2.1. The resultant precipitate was filtered, and was washed with aqueous hydrochloric acid (1M, 3×100 mL) and water to give Compound II-COOH as a pale pink solid (31.89 g, 52%). $^1$H NMR (300 MHz, DMSO)-$d_6$) δ: 7.74 (1H, dd), 7.38 (2H, d), 7.21 (3H, m), 6.67 (1H, m), 6.57 (1H, m), 2.48 (2H, t), 2.07 (2H, t), 1.71 (2H, m). Anal. Calcd for $C_{17}H_{17}NO_4$: C, 68.20 H, 5.73; N, 4.70. Found: C, 68.22; H. 5.61; N, 4.66.

Compounds VI-COON and VII-COOH may be prepared by this method using the appropriate starting materials.

Compound IV-COOH may be Prepared as Follows.

A slurry of 8-aminocaprylic acid (75.0 g, 0.471 mol) in methylene chloride (500 mL) was treated with chlorotrimethylsilane (102.34 g, 0.942 mol) and was heated to reflux for,2 hours. The reaction mixture was cooled to 0° C. and was then treated with triethylamine (142.98 g, 1.413 mol) followed by the dropwise addition of 4-methoxy-2-acetylbenzoyl chloride (107.71 g, 0.471 mol). The reaction mixture was stirred for 0.5 hours at OOC and then for 2 days at 25° C. Methylene chloride was removed in vacuo. NaOH solution (2N) was added to: the residue. This mixture was allowed to stir for 2 hr before the mixture was acidified to pH=1 with concentrated hydrochloric acid. The resulting solid was recovered by filtration and recrystalized in methylene chloride/hexane (1/1) several times. The structure was confirmed by $^1$H NMR. 38% Yield clean product. 8-N-(4-methoxysalicyloyl)aminocaprylic acid (59.58 g, 0.193 mol) Compound V-COOH may be Prepared as Follows.

1,8-Diaminooctane (1.44 g, 10 mmol) was dissolved in 50 ml of tetrahydrofuran (THF). To the solution was added dropwise succinic anhydride (1.0 g, 10 mmol) in 20 ml of THF at room temperature with stirring. A precipitate formed immediately. The reaction mixture was stirred for another 30 min. after addition. The precipitate was collected by filtration, washed thoroughly with THF and dried in air. It was dissolved in 10 ml of water at pH 10. The pH was then adjusted to 1 with 1N HCl water solution. The precipitate was filtered off. The filtrate was lyophilized to give a solid powder, which was then extracted with ethanol. Evaporation of ethanol gave 8-aminooctylsuccinic monoamide hydrogen chloride 2.2 g (78%), which was used for next reaction without further purification. 8-Aminooctylsuccinic monoamide hydrogen chloride (2.2 g, 7.8 mmol) was dissolved in 25 ml of IN NaOH water solution. To the solution was added O-acetylsalicyloyl chloride (1.55 g, 7.8 mmol) in three portions over a 2 hour period at room temperature with stirring. The mixture was stirred for another 2 hours. The pH of the reaction mixture was adjusted to 7. The precipitate formed was filtered off. The pH of the filtrate was then adjusted to 2. The solution was kept at room temperature for 2 hours. The precipitate was collected by filtration and dried in air. It was purified by recrystallization from ethanol/water, yield 1.5 g (55%) 8-Salicyloylaminooctyl succinic monoamide compound V-COOH, m.p. 123–125° C. Its structure was confirmed by reverse phase HPLC ($t_R$=4.3 min.), elemental analysis and $^1$H NMR. Elemental Analysis for $C_{19}H_{28}N_2O_5$: Calculated: C, 62.63, H, 7.69, N, 7.69; Found: C, 62.84, H, 7.60, N, 7.60. $^1$H NMR (300 MHz, DMSO-d6, ppm): 12.7 (br, 1H), 12.0(br, 1H), 8.8(t, 1H), 7.8(q, 1H), 7.35(h, 1H), 6.8(q, 2H), 3.2(m, 2H), 2.95(m, 2H), 2.35(t, 2H), 2.2(t, 2H), 1.5(m,2H) and 1.2(m, 10H).

Compunds X-COOH and XI-COOH are commercially available from Aldrich (Milwaukee, Wis.).

EXAMPLE 3

Preparation of Conjugate 1

Acryloyl chloride (45 ml) was added dropwise to a solution of N-hydroxysuccinimide (57.6 g) in 77 ml of triethylamine and 750 ml of chloroform at 0° C. over 40 minutes. The reaction mixture was stirred for an additional 40 minutes at room temperature, and then was washed with 300 ml of ice water and 300 ml of saturated NaCl solution. The organic layer was dried over anhydrous sodium sulfate in the presence of 50 mg of 4-butylpyrocatechol. After filtration, the filtrate was evaporated to 100 ml, to which 350 ml of n-hexane/ethyl acetate (6:1) was added with vigorous stirring to precipitate the product. The mixture was refrigerated overnight, and the precipitate was filtered and dried in vacuo. Recrystallization from ethyl acetate/hexane (1:1) gave 55 g of pure product N-acryloxysuccinimide, m.p. 69–70° C. An additional 12 g of the product was isolated from the mother liquor. The total yield was 91%.

15 g (0.89 mol) of product N-acryloxysuccinimide and 81 mg AIBN (2,2'-azobisisobutyronitrile) (0.49 mmol) were dissolved in 100 ml of benzene. Nitrogen gas was bubbled through the solution for 10 minutes and the flask was sealed. The reaction mixture was placed in an oil bath at 60° C. for 24 hours. The polymer precipitate was filtered, washed with benzene, and dried in vacuo. The yield of poly(N-acryloxysuccinimide) was 15 g (quantitative).

3.75 g (22 mmol) of product poly;(N-acryloxysuccinimide) was dissolved in 55 ml of DMF (solution E). 0.8 g (2.6 mmol) of N-(5-aminomethylsalicyloyl)-8-aminocaprylic acid prepared as in Example 1 were dissolved at 60–70° C. in 55 ml DMF and 0.52 g of triethylamine (solution F). The warm solution F was added gradually to solution E and the mixture was stirred at room temperature for 24 hours. The polymer conjugate of poly(N-acryloxysuccinimide) and N-(5-aminomethylsalicyloyl)-8-aminocaprylic acid ("unhydrolyzed polymer conjugate") was precipitated with dilute 0.1N HCl and collected by centrifugation. Then, unhydrolyzed polymer conjugate was hydrolyzed in 40 ml of 4% NaHCO, solution for 48 hours at room temperature and dialyzed against water for 48 hours using Spectra/Por dialysis membrane (MW cut-off 1000) (Spectrum Inc., Laguna Hills, Calif.). The solution was lyophilized and dried to give 2.23 g (85%) of conjugate 1 (I-COOH)-5-$CH_2$N-PAA. No low molecular weight compounds were found with SEC analysis. Mw=225,300, Mn=131,300, Mw/Mn=1.72. The nitrogen content in the conjugate was 1.39%, which corresponds to 14.7% of the delivery agent in the conjugate.

EXAMPLE 4

Preparation of Conjugate 2

(II-COOH)-5-$CH_2$NH-PAA conjugate was prepared by the method outlined in Example 3, except that N-(5-aminomethylsalicyloyl)-4-(4-aminophenyl)butyric acid from Example 2 was used in place of the product from Example 1, and after conjugation the polymer was precipitated with 2% NaHCO$_3$ solution (rather than 0.1N HCl). The yield was 80%. SEC analysis: Mw=210,900, Mn=118,600, Mw/Mn=1.79. The nitrogen content of the conjugate was 0.95% or 12% of the delivery agent in the conjugate.

EXAMPLE 5

Preparation of Conjugate 3

Alternating cc-polymer of M-PEG allyl ether and maleic anhydride available from Shearwater Polymers, Inc. (Huntsville, Ala.) was used. The co-polymer has an average molecular weight of PEG chain in the co-polymer unit of about 1500 D, and a total molecular weight of 14,000 D. 2.45 g of the co-polymer was dissolved in 30 ml of DMF. 464 mg of the product from Example 1 (I-COOH-5-$CH_2NH_2$) was dissolved in 70 ml of DMF where 2 ml $Et_3N$ have been added, and both solutions were mixed together and stirred at room temperature for 24 hours. The reaction was monitored by HPLC analysis. Then the solution was reduced in vacuo. The solid was dissolved in 100 ml of water and the pH of the solution was adjusted to 10.5–11.0. This solution was dialysed against water ($Mw_{cutoff}$=3,000) for a total of 72 hours. 2.05 g (70%) of (I-COOH)-5-$C_2$NH-PEG/maleic anhydride was obtained. The final product was analyzed by reverse phase HPLC, SEC and NMR Based on HPLC data, it contained no more than 1.5% of the product from Example 1. SEC data: $M_w$ 20,100 $M_n$ 11, 200 Mw/Mn 1.79. The nitrogen content in the conjugate was 1.07% or 10.5% w/w of the delivery agent bound to the polymer.

EXAMPLE 6

Poly(ethyleneglycol) [PEG]-Delivery Agent Conjugates Prepared via Esterification Reaction A number of PE-delivery agent conjugates of different molecular weight an functionality have been prepared using linear mono- and dihydroxy terminated PEG MW=200–4, 500 and branched polyfunctional PEG of molecular weight 1,770 and 10,000 available from Shearwater Polymers, Inc. (Huntsville, Ala.). The examples of the structures of PE and the delivery agents used for the esterification reaction are indicated below:

PEG linear: HO—(CH$_2$CH$_2$—O)$_m$—R m=4–100, R=H, OCH$_3$

PEG branched (8 arms):

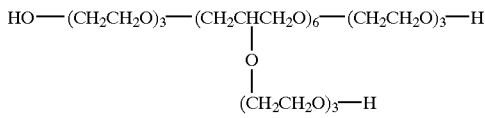

Example 6a. The reaction was carried out in a 0.5 L round bottom flask equipped with a condenser and a Dean-Stark trap. 30 g of PEG MW=300 (Carbowax 300) and 5 g of I-COOH were dissolved in 175 mL of toluene. 0.6 g of the catalyst p-toluene sulfonic acid monohydrate was added. The solution was refluxed for 30–40 min. and then a second portion of I-COOH (5 g) was added. The reaction was monitored by, reverse phase HPLC and was stopped when only 3–5% of non-reacting I-COOH was found on the chromatogram. This normally takes 3–4 hours, and in this case took approximately 3 hours. The solution was cooled to room temperature and poured into 750 mL of slightly basic water (pH=7.5–8.0 adjusted with NaHCO$_3$ saturated solution) and was left for 3–4 hours in the separation funnel. Three layers formed: a top toluene layer, an intermediate water layer and a bottom layer containing the target conjugate. The bottom layer was separated and was reduced under vacuum. 13.2 g (63%) of oily product was obtained. NMR confirmed the conjugate's structure: ~COOCH$_2$— δ=4.13 ppm(tripl.) and the absence of COOH group. The content of nitrogen was 2.54% (calculated 2.53%). The calculated molecular weight of the conjugate is ~600. The structure of the conjugate is shown below.

I-COO—CH$_2$CH$_2$O(CH$_2$CH$_2$O)$_5$CH$_2$CH$_2$OH conjugate 4

The following conjugates were prepared by the same method using the appropriate starting materials. The molecular weights of the PEG are given in parentheses. Conjugates 14(300), 15(300), 16(400), 24(350), 25(550), 26(350), 27(400), 28(300), 29(400), 32(2,000), 33(600), 35(10,000), 36(10,000), 37(10,000), 38(10,000), 39(2,000) (the product precipitated out in a separation funnel), 41(300) (the product precipitated out in a separation funnel), 42(300), 43(550), 44(600), 45(1,000), 46(1,000), 47(600), were prepared by this method with appropriate starting materials.

Example 6b. The same procedure as in 6a was used to prepare a conjugate based on Carbowax200 and the delivery agent I-COOH. The yield of the conjugate was 67%. Nitrogen content was 3.01%. The calculated molecular weight is 470 D. The structure is shown below.

I-COO—CH$_2$CH$_2$O(CH$_2$CH$_2$O)$_3$CH$_2$CH$_2$OH Conjugate 5

Example 6c. The reaction was carried out using the same equipment as in 6a. 5.6 g of poly(ethylene glycol) methyl ether MW=350 (Aldrich) and 3.6 g of I-COOH were dissolved in 80 mL of toluene. 0.3 g of analyst p-toluene sulfonic acid monohydrate was added. The solution was refluxed for 3 hours The solution was then cooled to room temperature and transferred into a separation funnel A mixture of 53 mL of water and 7 mL of saturated solution of NaHCO$_3$ were added. The top toluene layer was separated, washed with water and reduced under vacuum. The final product was a viscous oil, yield was 92%, and nitrogen content was 2.25%. The calculated molecular weight is 620 D. The structure is shown below:

I-COO—CH$_2$CH$_2$O(CH$_2$CH$_2$O)$_5$CH$_2$CH$_2$OH$_3$ Conjugate 6

The following conjugates were prepared by the same method using the appropriate starting materials. The molecular weights of the PEG methyl ether are given in parentheses Conjugates 13(750), 21(550), 40 (1,900) and 48 (350).

Example 6d. The same procedure as in 6a was used to prepare a conjugate based on Carbowax400 and the delivery agent I-COOH. The yield of the conjugate was 63%. Nitrogen content was 2.4%. The calculated molecular weight is 700 D. The structure is shown below.

I-COO—CH$_2$CH$_2$O(CH$_2$CH$_2$O)$_7$CH$_2$CH$_2$OH Conjugate 7

Example 6e. The same procedure as in 6a was used to prepare a conjugate based on Carbowax300 (PEG MW=300) and delivery agent II-COOH. The yield of the conjugate was 65%, nitrogen content-2.06. The calculated molecular weight is 600 D. The structure is shown below:

II-COO—CH$_2$CH$_2$O(CH$_2$CH$_2$O)$_5$CH$_2$CH$_2$OH Conjugate 8

Conjugates 19 and 20 were prepared by this same method except that PEG methyl ether with MW=550 and MW=350, respectively, was used instead of PEG MW=300.

Example 6f. The same procedure as in 6a was used to prepare a conjugate based on Carbowax400 and the delivery agent III-COOH. The yield of the conjugate was 61i. Nitrogen content was 1.98%. The calculated molecular weight is 700. The structure is shown below.

III-COO—CH$_2$CH$_2$O(CH$_2$CH$_2$O)$_7$CH$_2$CH$_2$OH Conjugate 9

Example 6 g. The same procedure as in 6a was used to prepare a conjugate based on Carbowax600 and the delivery agent I-COOH. The yield of the conjugate was 71%. Nitrogen content was 1.05%. The calculated molecular weight is 900. The structure is shown below.

I-COO—CH$_2$CH$_2$O(CH$_2$CH$_2$O)$_{11}$CH$_2$CH$_2$OH Conjugate 10

Example 6h. 15.0 g (0.0065 equiv.) of PEG MW=4600 ("Carbowax 4600NF"), 1.65 g (0.0058 equiv.) I-COOH and 0.45 g of p-toluene sulfonic acid monohydrate were dissolved in 120 mL of toluene. The reaction mixture was refluxed for 13 hours. The reaction was monitored by HELC and was stopped when a negligible amount of non-reacting I-COOH remained. The solution was reduced under vacuum. 15.3 g (92!k) of solid waxy product was recovered. The conjugate was identified by NMR, HPLC and elemental analysis (N—0.43%). The calculated molecular weight is 5,100. This conjugate has the structure below:

I-COO—CH$_2$CH$_2$O(CH$_2$CH$_2$O)$_{102}$CH$_2$CH$_2$—OOC-I Conjugate 11

Example 6i. 6.3 g of branched 8 arms PEG2000 (actual MW=1770), 4.0 g I-COOH and 0.2 g of p-toluenet sulfonic acid monohydrate was refluxed in 30 mL of toluene for 2.5 hours. 9.9 g of a viscous oily product was obtained after toluene evaporation. Based on HPLC data, the conjugate was found a to contain only a negligible amount of non-reacting original I-COOH. NMR spectrum shows the presence of an ester group (δ=4.2 ppm) and confirms the absence of carboxyl groups in the conjugate. The yield was 85% and the Nitrogen content was 0.62%. The calculated molecular weight is 2800. The compound I-COO is attached at the PEG-OH group through an ester linkage at 4 of the 8 "arms". The conjugate is denoted "Conjugate 12".

EXAMPLE 7

Preparation of Compound I-CH$_2$NH$_2$ and its Hydrogen Chloride Salt

O-Acetylsalicylic acid (36 g, 0.2 mol) and N-hydroxysuccinimide (23 g, 0.2 mol) were dissolved in 200 ml of DMF. 1,3-Dicyclohexylcarbodiimide (40.5 g, 0.2 mol) in 50 ml of chloroform was added dropwise to the solution at 0° C. with stirring. The mixture was stirred for another 20 h at room temperature. The precipitate was filtered off. Evaporation of the filtrate under reduced pressure gave a syrupy residue It was re-dissolved in 200 ml of chloroform. The solution was kept in freezer for 2 h. The precipitate was again filtered off The filtrate was washed with 4% sodium bicarbonate (200 ml×3), 10% NaCl (200 ml×2), 0.1N HCl (200 ml×2) and 10% NaCl (200 ml×2) water solutions, respectively. It was dried over anhydrous sodium sulfate. Evaporation of chloroform gave a syrupy product (50 g, 90%), which solidified after being dried in vacuo overnight.

The active ester obtained above (25 g, 90 mmol) in 150 ml of methylene chloride was added dropwise to a solution of 1,8-diaminooctane (26 g, 180 mmol) in 500 ml of methylene chloride over a period of 2 to 3 h (one drop per second) The mixture was stirred for an additional 15 h. The precipitate was collected by filtration, washed with methylene chloride and dried in air. It was extracted with 300 ml of 0.1N HCl water solution for 30 min. with stirring. The insoluble substance was filtered off. The filtrate was adjusted to pH 8 to 9 with 40% sodium hydroxide. Precipitation occurred at this point. It was kept at room temperature for 3 h. The precipitate was collected by filtration. It was dried thoroughly in air, yield 10 g(42%), m.p, 155–156° C. This compound can be further purified by recrystallization from ethanol or water. Reverse phase HPLC: $t_R$=2.85 min. $^1$H NMR (300 MHz, DMSO-d6), δ (ppm): 1.25 (8H, m), 1.45 (4H, m), 2.1(2H, t), 3.2 (2H, m), 6.45 (1H, h), 6 6 (1H, q), 7.1 (1H, h), 7.7 (1H, q), 6.5 (3H, br), 10.8 (1H, br). Elemental analysis for C$_{15}$H$_{24}$O$_2$N$_2$ (+0.25H2O): calculated: C, 67.04, H, 9.12, N, 10.43; found: C, 67.13, H, 9.37, N, 10.64. The water content was determined by KF (0.25%).

The product from above Compound I-CH$_2$NH$_2$ (0.3 g, 1.1 mmol) was dissolved in 10 ml of warm (about 50° C.,) anhydrous ethanol. Anhydrous hydrogen chloride gas was bubbled through the solution for 10 min. Dry air was then passed through the solution for 10 min. Evaporation of the solvent gave a solid residue, which was recrystallized from EtOH/Et$_2$O to give the hydrogen chloride salt of Compound I-CH$_2$NH$_2$ (0.31 g, 91%), m.p.119–121° C. Reverse HPLC: $t_R$=2.9 min.; $^1$H NMR (300 MHz, DMSO-d6), δ (ppm): 1.2 (8H, m), 1.5 (4H, m), 2.7 (2H, m), 3.2 (2H, m), 6.85 (2H, m), 7.35 (1H, h), 7.8(1H, q), 7.9(3H, br), 8.9 (1H, t), 12.7 (1H, br). Elemental analysis for C$_{15}$H$_{25}$O$_2$N$_2$Cl: calculated: C, 59.90, H, 8.32, N, 9.32; found C, 60.02, H, 8.21, N, 9.28.

EXAMPLE 8

Preparation of Conjugate 17

Monomethoxy polyethylene glycol 350 (2 g, 5.7 mmol) was dissolved in 20 ml of methylene chloride containing 4 ml of pyridine. To this solution were added 1.2 g (5 8 mmol) of 4-nitrophenylchloroformate and 85 mg of 4-dimethylaminopyridine as catalyst at 0° C. The reaction mixture was stirred for 2 h at 0° C. and another 2 h at room temperature. The reaction was monitored with reverse phase HPLC. Evaporation of methylene chloride gave the syrupy product, which was used directly for the next step reaction without further purification.

1-N-Salicyloyl-1,8-diaminooctane (1.5 g, 5.7 mmol) prepared as above in Example 7 was dissolved in 25 ml of 70–80° C. pyridine. The solution was mixed with the p-nitrophenyl monomethoxy polyethylene glycol 350 carbonate obtained from the previous reaction. The reaction mixture was stirred at room temperature for 50 h. Evaporation of pyridine under reduced pressure gave a syrupy raw product It was dissolved in 200 ml of methylene chloride. The solution was washed with 0.1N HCl (200 ml×3), 10% NaCl (200 ml×2), 4% sodium bicarbonate (200 ml×3) and 10% NaCl (200 ml×2) water solutions. It was dried over anhydrous sodium sulfate. Reverse phase HPLC was used to monitor both the reaction and the work-up process. Evaporation of methylene chloride gave the product 1.9 g (53%). The structure was confirmed by reverse phase HPLC ($t_R$= 5.43 min.), N analysis (the calculated value is 4.32%, the found value was 4.04%) and NMR. A new triplet peak for one amide proton was observed at 7.2 ppm; the chemical shift of methylene proton linked to the free amino group of the starting material shifted from 2.6 ppm to 3.0 ppm when the amino group was converted to the urethane. The calculated molecular weight is 640.

Conjugate 34 was also prepared,by this method using the product as prepared in Example 1 and PEG MW=2,000.

EXAMPLE 9

Preparation of Conjugate 18

Monomethoxy polyethylene glycol 350 (3.5 g, 10 mmol) was dissolved in 20 ml of chloroform containing 1.8 g (18 mmol) of triethylamine. To this solution, 2.0 g of tosyl chloride (10.5 mmol) was added with stirring. The reaction mixture was stirred overnight at room temperature. The precipitate was filtered off. The filtrate was diluted with 100 ml of chloroform. The solution was then washed with 0.1N HCl (100 ml×3), 10% NaCl (100 ml×2), 4% sodium bicarbonate (100 ml×2) and 10% NaCl (100 ml×2) water solutions. The chloroform layer was dried over anhydrous sodium sulfate. Evaporation of chloroform gave the tosylated monomethoxy polyethylene glycol 350, which was used for the following reaction.

1-N-Salicyloyl-1,8-diaminooctane (2.64 g, 10 mmol), D32, was dissolved in 30 ml of 70–80° C. pyridine. To this solution, the tosylated monomethoxy polyethylene glycol 350 obtained from the previous reaction in 20 ml of pyridine was added dropwise over 40 minutes with stirring. The reaction was stirred at 70° C. for 5 h and at room temperature overnight. The precipitate was filtered off. The filtrate was evaporated under reduced pressure to dryness to give a syrup raw product, which was dissolved in 150 ml of methylene chloride. The solution was washed with 0.1N HCl (150 ml×3) and 10% NaCl (150 ml×2) water solutions. The methylene chloride solution was collected and dried over anhydrous sodium sulfate. After evaporation of methylene chloride, an oily substance was obtained. It was then dissolved in 200 ml of water. The milk solution obtained became clear after extraction with diethyl ether five times (200 ml×5). The clear water solution was then extracted with 200 ml of methylene chloride. The methylene chloride layer was collected and dried over anhydrous sodium sulfate. Both the reaction and the work-up process were monitored by reverse phase HPLC. Evaporation of methylene chloride gave the product 0.8 g (29%). The structure was confirmed by reverse phase HPLC ($t_R$=3.73 min.), N analysis (the calculated value is 3.65%, the found value was 3.39%) and NMR. The peak of two protons of amine salt was observed at 8.5 ppm. Four aromatic protons of p-toluenesulfonic acid were found at 7.1 ppm and 7.5 ppm. Two methylene protons of the methylene, group linked to the free amino group of the starting material shifted from 2.6 ppm to 3.6 ppm when the amino group was converted to the p-toluenesulfonic acid salt form. The calculated molecular weight is 768.

EXAMPLE 10

Preparation of Conjugate 22

2-(monomethoxy polyethylene glycol 350)acetic acid (MW=350) (12.0 g, 29.4 mmol) in 50 ml of methylene chloride was added in a solution of 4.0 g (35 mmol) of N-hydroxysuccinimide in 8 ml of DMF and 20 ml of methylene chloride. To this solution, 7.4 g (36 mmol) of DCC in 30 ml of methylene chloride was added. The reaction mixture was stirred at room temperature for 24 h. The precipitate was filtered off. The filtrate was kept in the freezer for 2 h. Again the precipitate was filtered off. The filtrate was diluted with 100 ml of methylene chloride. The solution was washed with 0.1N HCl (200 ml×3), 10% NaCl (200 ml×2), 4% sodium bicarbonate (200 ml×3) and 10% NaCl (200 ml×2) water solutions and dried over anhydrous sodium sulfate. Evaporation of methylene chloride gave the PEG acetic acid active ester intermediate 8.8 g (58%), which was used for the following reaction without further purification.

1-N-Salicyloyl-1,8-diaminooctane (3.6 g, 13.6 mmol) was dissolved in 45 ml of 70–80° C. pyridine. To the solution was added 6.9 g (13.6 mmol) of the PEG acetic acid active ester prepared above. The reaction mixture was stirred under nitrogen atmosphere for 4 h at 70° C. It was then kept at room temperature overnight. Reverse phase HPLC was used to monitored the reaction. Evaporation of pyridine gave a syrupy raw product. It was dissolved in 200 ml of methylene chloride. The solution was washed with 0.1N HCl (200 ml×3), 10% NaCl (200 ml×2), 4% sodium bicarbonate. (200 ml×3) and 10% NaCl (200 ml×2) water solutions. The methylene chloride solution was collected and dried over anhydrous sodium sulfate. Evaporation of methylene chloride gave the syrupy product (6.6 g, 74%), which was further purified as follows. The syrupy product was dissolved in 200 ml of distilled water. The solution was refrigerated (5–10° C.) overnight The precipitate was then carefully filtered off until a clear filtrate was obtained. The solution was extracted with 100 ml of methylene chloride twice The methylene chloride solution was dried over anhydrous sodium sulfate. Evaporation of methylene chloride gave the product 6.3 g. Trace amount of methylene chloride was removed from the syrupy product by bubbling nitrogen through the product. The chemical structure was confirmed by reverse phase HPLC ($t_R$=4.6 min.), nitrogen analysis (the calculated value is 4.28%, the found value was 4.18) and NMR. A new triplet peak for one amide proton was observed at 7.65 ppm. The chemical shift of methylene proton linked to the free amino group of the starting material shifted from 2.6 ppm to 3.1 ppm when the amino group was converted, to the amide. The calculated molecular weight is 654.

Conjugate 23 was also prepared by this method except that 2-(monomethoxy polyethylene glycol, 550) acetic acid (MW=550) was used instead of the MW=350 material.

Conjugate 30 was also prepared by this method except that the starting materials were 2-(monomethoxy polyethylene glycol 350) acetic acid and the product from Example 1 (I-COOH)-5-$CH_2$-$NH_2$) (instead of 1-N-salicyloyl-1,8-diaminooctane).

EXAMPLE 11

Preparation of Conjugate 31

5.0 g (18.9 mmol) of 1-N-salicyloyl-1,8-diaminooctane (Compound I-$CH_2NH_2$) prepared as in Example 7 was dissolved in 100 mL of 90–100° C. pyridine, and then cooled to room temperature. The resulting suspension of N-salicyloyl-1,8-diaminooctane was added by pipet to 5.73 g(28.4 mmol) of 4-nitrophenyl chloroformate dissolved in 100 mL of pyridine and stirred for 15 minutes. The solvent was removed by evaporation leaving a red oil with precipitate. The oil was dissolved in 100 mL of dichloromethane and the precipitate was filtered off. The dichloromethane solution was washed with 0.1 N HCl (100 mL,three times), 5% sodium bicarbonate solution (75 mL, three times), dried over sodium sulfate and evaporated to yield 4.3 g of an orange-brown solid at 53% yield of N-(4-oxycarbonyl-nitrobenzene)-N-Salicyloyl-1,8-diaminooctane.

The above product was then reacted with methoxypoly (oxyethylene/oxypropylene)-2-propylamine HTJ-506 manufactured by Huntsman (Houston, Tex.) (hereafter referred to as methoxyPEG$_{1,000}$-$NH_2$) 1.95 g (4.54 mmol) of the above product was dissolved in 20 mL of acetonitrile and a precipitate (approx. 220 mg) was filtered off. The solution was added to 4.90 g (4.55 mmol) methoxyPEG$_{1,000}$-$NH_2$), dissolved in 20 mL of acetonitrile. The reaction was monitored with HPLC and completed after 3.5 hours at room temperature. The solvent was removed by evaporation and 6.4 g of a yellow-orange oil was found. The oil was dissolved in 40 mL of dichloromethane. This solution was washed twice with 50 mL of 0.1N HCl (to remove unreacted methoxyPEG$_{1,000}$-$NH_2$,) once with 10%NaCl solution, and continuously washed with 50 mL portions of 5% sodium bicarbonate solution until 4-nitrophenyl was removed (as detected by reverse phase HPLC). The solution was dried over sodium sulfate and evaporated to yield 3.5 g of a yellow-orange solid This solid was then dissolved in 50 mL of distilled water and washed with 30 mL of diethyl ether. The water layer was collected and the final product was extracted from water with dichloromethane, dried over sodium sulfate and evaporated to yield 3.1 g of a yellow-orange wax at 57% yield of Conjugate 31. It has been named N-PEG-N'-(N-salicyloyl)-heptylamine urea. The purity and structure was confirmed by reverse phase HPLC, elemental analysis (calculated value of N is 3.02%, found 3.09%) and NMR. Two new multiplet peaks at δ=5.57 ppm and 5.79 ppm of equal intensity which are characteristic for substituted ureas were observed, and the peak of methylene proton next to amino group of starting material at 2.6 ppm disappeared. The calculated MW is ~1400.

EXAMPLE 12

Recombinant Human Growth Hormone (rhGH)
Oral/Intracolonic Delivery

Oral gavage (PO) and/or intracolonic (IC) dosing solutions of delivery agent compound and rhGH in water, phosphate buffer (PE) or 5% aqueous ethanol were prepared. Typically, a solution of the conjugate was prepared by mixing in water and stirred. The final dosing solutions were prepared by mixing the conjugate solution with an rhGH stock solution (typically 15 mg rhGH/ml) and diluting to the desired volume (usually 3.0 ml). The compounds and rhGH dose amounts are listed below in Table 1.

Male Sprague-Dawley rats weighing between 200–250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO), an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm Rusch catheter tube (French 8 or 6) was adapted to a syringe with an Eppendorf pipette tip. The syringe was filled with the 0.5 ml dosing solution by drawing the solution through the catheter tube. The catheter tube was wiped dry. K-Y jelly was applied to the tip, avoiding contact with the eye of the tube, and the tube was inserted to the colon through the anus until the tube was no longer visible. The solution was injected by pressing the syringe plunger, and the tube was removed.

Blood samples were collected serially from the tail artery, typically eat time=0, 15, 30, 45, 60 and 90 minutes for oral and 0, 10, 20, 30, 60 and 90 for IC dosing. Serum rHGH concentrations were quantified byran rHGH immunoassay test kit (Kit # K1F4015 from. Genzyme Corporation Inc., Cambridge, Mass.). Previous studies indicated baseline values of about zero.

The results of PO administration are presented in Table 1 below wherein rhGH was administered with (a) delivery agent I alone, (b) Conjugate 1, and (c) Conjugate 3. The experiments were performed at 1/10 the delivery agent concentration versus that of the conjugate. Thus, at a dose of 200 mg/kg conjugate, the actual amount of delivery agent dosed was 20 mg/kg With such a concentration of delivery agent complexed with polymer there was evidence of systemic delivery.

Dose volume for IC administration was 1 ml/kg. rhGH dose was 1 mg/kg. For IC dosing, the five samples from each time period were pooled and the maximum concentration for each group (Cmax) are reported below in Table 2.

TABLE 2

Intracolonic Delivery of rhGH in Rats

| Conjugate | Dosing solution medium | Conjugate Dose (mg/kg) | rhGH Dose (mg/kg) | Mean Peak Serum [rhGH] (ng/ml) ± SD |
|---|---|---|---|---|
| 1 | PB | 25 | 1 | 16 ± 9 |
| 1 | PB | 25 | 1 | 1 ± 2 |
| 3 | PB | 25 | 1 | 14 ± 34 |
| 4 | PB | 25 | 1 | 6 ± 16 |
| 4 | 5% aq. EtOH | 25 | 1 | 182 ± 18 |
| 4 | 5% aq. EtOH | 61 | 1 | 172 ± 29 |
| 6 | 5% aq. EtOH | 25 | 1 | 168 ± 54 |
| 7 | 5% aq. EtOH | 25 | 1 | 205 ± 95 |
| 8 | 5% aq. EtOH | 25 | 1 | 101 ± 32 |
| 10 | water | 120 | 1 | 30 ± 23 |
| 10 | PB | 25 | 1 | 0.5 ± 1.0 |
| 12 | 5% aq. EtOH | 25 | 1 | 0 |
| 13 | 5% aq. EtOH | 25 | 1 | 63 ± 43 |
| 14 | 5% aq. EtOH | 25 | 1 | 75 ± 35 |
| 17 | 5% aq. EtOH | 25 | 1 | 136 ± 37 |
| 18 | 5% aq. EtOH | 25 | 1 | 140 ± 51 |
| 22 | 5% aq. EtOH | 25 | 1 | 164 ± 53 |
| 24 | PB | 25 | 1 | 0 |
| 25 | PB | 25 | 1 | 0 |

TABLE 1

Oral Administration of rhGH

| Rat. | Group | Base line | Min15 | Min30 | Min45 | Min60 | Min90 |
|---|---|---|---|---|---|---|---|
| 1 | 7625-1 | (a) | 0 | 84.73 | 13.19 | 0 | 10.565 | 0 |
| 2 | -2 | (a) | 0 | 79.98 | 22.69 | 0 | 5.49 | 0 |
| 3 | -3 | (a) | 0 | 48.72 | 1.82 | 0 | 7.905 | 0 |
| 4 | -4 | (a) | 0 | 45.34 | 46.52 | 35.53 | 34.885 | 2.715 |
| 5 | -5 | (a) | 0 | 0 | 58.44 | 0 | 3.922 | 0 |
| 6 | 7626-1 | (a) | 0 | 64.2 | 18.99 | 4.29 | 10.13 | 0 |
| 7 | -2 | (a) | 0 | 43.14 | 23.44 | 18.35 | 15.93 | 1.47 |
| 8 | -3 | (b) | 0 | 6.16 | 0 | 0 | 4.92 | 0 |
| 9 | -4 | (b) | 0 | 30.71 | 0 | 0 | 10.025 | 0 |
| 10 | -5 | (b) | 0 | 26.15 | 0 | 0 | 9.985 | 0 |
| 11 | 7627-1 | (b) | 0 | 5.35 | 0 | 0 | 4.28 | 0 |
| 12 | -2 | (b) | 0 | 14.99 | 0 | 0 | 3.39 | 0 |
| 13 | -3 | (b) | 0 | 13.74 | 0 | 0 | 6.075 | 0 |
| 14 | -4 | (b) | 0 | 16.05 | 0 | 0 | 21.495 | 0 |
| 15 | -5 | (c) | 0 | 14.42 | 0.1 | 0 | 11.26 | 0 |
| 16 | 7628-1 | (c) | 0 | 7.87 | 0 | 0 | 15.19 | 0 |
| 17 | -2 | (c) | 0 | 14.31 | 0 | 0 | 17.545 | 0 |
| 18 | -3 | (c) | 0 | 0 | 3.57 | 0 | 4.745 | 0 |
| 19 | -4 | (c) | 0 | 28.76 | 83.12 | 0 | 2.78 | 0 |
| 20 | -5 | (c) | 0 | 5.08 | 0 | 0 | 0.235 | 0 |

EXAMPLE 13

Parathyroid Hormone Delivery (PTH 1–34)

Oral/Intracolonic Delivery

Oral gavage (PO) and/or intracolonic (IC) dosing solutions of delivery agent compound and human parathyroid hormone residues 1–34 (PTH) in water and varous aqueous solutions as indicated in the Table 3 below (PEG 300 and PEG 350 is available from Aldrich, (Milwaukee, Wis.) Kollidon 17PP is polyvinyl-pyrrolidone available from Aldrich. PG is propylene glycol). Typically, a solution of the conjugate was prepared in the appropriate medium and stirred The final dosing solutions were prepared by mixing the conjugate solution with a PTH stock solution (typically 5 mg PTH/ml) and diluting to the desired volume (usually 3.0 ml). The final compound, PTH and volume dose amounts, and the dosing medium used are listed below in Table 3.

Male Sprague-Dawley rats weighing between 200–250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO), an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm Rusch catheter tube (French 8 or 6) was adapted to a syringe with an Eppendorf pipette tip. The syringe was filled with the dosing solution by drawing the solution through the catheter tube The catheter tube was wiped dry. K-Y jelly was applied to the tip, avoiding contact with the eye of the tube, and the tube was inserted into the colon through the anus until the tube was no longer visible. The solution was injected by pressing the syringe plunger, and the tube was removed.

Blood samples were collected serially from the tail artery, typically at time=0, 15, 30, 45, 60 and 90 minutes for oral and 0, 10, 20, 30, 60 and 90 minutes for IC dosing. Serum PTH concentrations were quantified by a PTH radioimmunoassay kit (Kit # RIK 6101 from Peninsula Laboratories, Inc., San Carlos, Calif.). Previous studies indicated baseline values of about zero. Results from the five rats in each group were averaged for each time point. The maximum and the area under the curve, (AUC) are reported below in Table 3.

TABLE 3

Oral/Intracolonic Delivery of PTH in Rats

| Conjugate | Method of Administration | dosing medium (in water) | Volume dose (ml/kg) | Conjugate Dose (mg/kg) | PTH Dose ($\mu$g/kg) | Mean Peak Serum [PTH] (pg/ml) ± SE | AUC |
|---|---|---|---|---|---|---|---|
| 4 | PO | 10% EtOH | 1 | 100 | 200 | 86 ± 86 | 1285 |
| 4 | PO | 10% PEG300 | 1 | 100 | 200 | 39 ± 27 | 1694 |
| 4 | PO | 15% Kollidon 17PF | 1 | 100 | 200 | 44 ± 44 | 780 |
| 4 | PO | 10% PEG300 | 1 | 150 | 200 | 122 ± 60 | 3520 |
| 4 | PO | 5% EtOH |  | 150 | 200 | 36 ± 32 | 1184 |
| 4 | PO | 15% Kollidon 17PF | 1 | 150 | 200 | 126 ± 123 | 3684 |
| 4 | PO | 10% PEG300 | 1 | 300 | 200 | 418 ± 290 | 9315 |
| 4 | PO | 5% EtOH | 1 | 300 | 200 | 94 ± 27 | 2627 |
| 4 | PO | 15% Kollidon 17PF | 1 | 300 | 200 | 298 ± 265 | 6276 |
| 4 | PO | 10% PEG300 | 1 | 300 | 200 | 87 ± 24 | 4165 |
| 4 | PO | 30% PEG300 | 1 | 300 | 200 | 106 ± 43 | 4572 |
| 14 | IC | 5% EtOH | 0.5 | 100 | 25 | 501 ± 34 | 16335 |
| 22 | PO | 5% citric acid (pH = 3.85) | 1 | 100 | 200 | 855 ± 511 | 27609 |
| 22 | PO | water (pH = 7.75) | 1 | 100 | 200 | 34 ± 13 | 1286 |
| 22 | PO | 5% NaHCO$_3$ (ph = 10.13) | 1 | 100 | 200 | 225 ± 171 | 10614 |
| 14 | PO | 5% EtOH | 1 | 250 | 200 | 320 ± 114 | 10933 |
| 16 | PO | 5% EtOH | 1 | 250 | 200 | 265 ± 47 | 9965 |
| 32 | PO | water | 1 | 100 | 200 | 246 ± 119 | 4426 |
| 22 | PO | 15% PEG350 | 1 | 100 | 200 | 3508 ± 267 | 249861 |
| 22 | PO | 15% PG | 1 | 100 | 200 | 2755 ± 537 | 242849 |
| 22 | PO | 15% Kollidon 17PF | 1 | 100 | 200 | 3173 ± 250 | 243838 |
| 22 | PO | water | 1 | 100 | 200 | 3577 ± 113 | 280258 |
| 22 | PO | 5% citric acid (pH = 2.78) | 1 | 100 | 200 | 946 ± 701 | 27117 |
| 22 | PO | 5% NaHCO$_3$ (pH = 10.04) | 1 | 100 | 200 | 899 ± 730 | 20245 |

TABLE 3-continued

Oral/Intracolonic Delivery of PTH in Rats

| Conjugate | Method of Administration | dosing medium (in water) | Volume dose (ml/kg) | Conjugate Dose (mg/kg) | PTH Dose (µg/kg) | Mean Peak Serum [PTH] (pg/ml) ± SE | AUC |
|---|---|---|---|---|---|---|---|
| 22 | PO | water (pH = 7.82) | 1 | 100 | 200 | 1678 ± 763 | 43639 |
| 22 | PO | water | 1 | 100 | 200 | 118 ± 112 | 5696 |
| 22 | PO | 15% PEG350 | 1 | 100 | 200 | 113 ± 55 | 5201 |
| 22 | PO | 15% PG | 1 | 100 | 200 | 273 ± 235 | 8193 |
| 22 | PO | 15% Kollidon 17PF | 1 | 100 | 200 | 126 ± 117 | 4993 |
| 24 | PO | 5% EtOH | 1 | 100 | 200 | 48 ± 32 | 2290 |
| 25 | PO | 5% EtOH | 1 | 100 | 200 | 287 ± 134 | 10486 |
| 30 | PO | 5% EtOH | 1 | 100 | 200 | 0 | 0 |
| 49 | PO | 5% EtOH | 1 | 100 | 200 | 73 ± 73 | 2785 |
| 49 | PO | 5% EtOH | 1 | 100 | 200 | 1467 ± 77 | 106705 |

PTH was also administered in capsules via PO and IC routes. Mini hard gel capsules (size 9) with a total volume 25 µL and manufactured by Torpac Inc.(Fairfield, N.J., USA) were used. For IC administration, 25 µg PTH/capsule and is mg/capsule conjugate 22 was used. For PO administration, 100 µg PTH/capsule and 20 mg/capsule conjugate 22 was used. The powder of PTH was mixed with the oily conjugate in a vial in the above-mentioned ratio. A clear solution resulted. Solution was added to capsules by syringe and weighed to reach the appropriate weight.

Capsules were administered as above, with the following changes. For PO dosing, a rat/hamster capsule dispenser (available from Torpac, Inc., Fairfield, N.J.) was marked 10 cm from the dosing end. The capsule was placed into the dispenser, which was inserted into the mouth and down the esophagus until the 10 cm mark meets the incisor teeth. The plunger was pushed and withdrawn. The dosing was optionally followed by administration of about 1.0 ml water (as in PO dosing of solutions). For IC dosing, a rat/hamster pill dispenser was marked 7.5 cm from the dosing end. The capsule was placed into the dispenser. A small amount of KY jelly was placed at the tip of the dispenser, and the dispenser inserted into the anus up to the 7.5 cm mark. The plunger was pressed and withdraw.

Results were obtained as above and are shown below in Table 4.

TABLE 4

Oral/Intracolonic Delivery of PTH in Rats

| Conjugate | Method of Administration | dosing medium (in water) | Dose | Conjugate Dose (mg/kg) | PTH Dose (µg/kg) | Mean Peak Serum [PTH] (pg/ml) ± SE | AUC |
|---|---|---|---|---|---|---|---|
| 22 | PO | capsule | 1 capsule | 20 | 100 | 2275 ± 916 | 242288 |
| 22 | IC | capsule | 1 capsule | 15 | 25 | 3438 ± 559 | 80928 |

EXAMPLE 3

Heparin Delivery

Intracolonic Delivery

Intracolonic (IC) dosing solutions containing a conjugate and heparin sodium USP in 25% aqueous propylene glycol were prepared Typically, the oily conjugate and powdered heparin (about 166–182 IU/mg) were dissolved in 25% v/v aqueous propylene glycol, vortexed and placed in a sonicator (about 37° C.). The pH was adjusted to about 7 (6.5 to 8.5) with aqueous NaOH (2N). The dosing solution was sonicated to produce a clear solution. The final volume was adjusted to 3.0 ml. The final conjugate dose, heparin dose and volume dose amounts are listed below in Table 5.

Male Sprague-Dawley rats weighing between 275–350 g were fasted for 24 hours and were anesthetized with ketamine hydrochloride (88 mg/kg) intramuscularly immediately prior to dosing. A dosing group of five rats was administered one of the dosing solutions. Por intracolonic (IC) dosing, a 7.5 cm, 8 fr Rusch catheter was adapted to a m ml syringe with a pipette tip. The dosing catheter was inserted into the colon through the anus until the tube was no longer visible. The dosing solution was expressed slowly into the colon.

Citrated blood samples were collected by cardiac puncture following the administration of ketamine (88 mg/kg), typically at time=0.25, 0.5, 1.0 and 1.5 hours. Reparin activity was determined by utilizing the activated partial thromboplastin time (APTT) according to the method of Henry, J. B., Clinical Diagnosis and Management by Laboratory Methods, Philadelphia, Pa., W. B. Saunders (1979). Previous studies indicated baseline values of about 20 sec. Results from the five rats in each group were averaged for each time point. The maximum is reported below in Table 5.

TABLE 5

Intracolonic Delivery of Heparin

| Conjugate | Method of Administration | volume dose (ml/kg) | Conjugate Dose (mg/kg) | Heparin Dose (mg/kg) | Mean Peak APTT (sec) ± SD |
|---|---|---|---|---|---|
| 4 | IC | 1 | 50 | 25 | 163 ± 149 |

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claims.

What is claimed is:

1. A polymeric delivery agent comprising a polymer conjugated to a modified amino acid or derivative thereof via a linkage group selected from the group consisting of —NHC(O)NH—, —C(O)NH—, —NHC(O)—, —OOC—, —COO—, —NHC(O)O—, —OC(O)NH—, —CH$_2$NH—, —NHCH$_2$—, —CH$_2$NHC(O)O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid, wherein the modified amino acids are acylated or sulfonated amino acids, ketones or aldehydes of acylated or sulfonated amino acids, salts thereof, or polyamino acids or polypeptides of any of the foregoing, and the polymer is selected from the group consisting of polyethylene; polyacrylates; polymethacrylates; poly(oxyethylene); poly(propylene); polypropylene glycol; polyethylene glycol (PEG); PEG-maleic anhydride copolymers; and derivatives and combinations thereof.

2. The polymeric delivery agent of claim 1 wherein the polymer has a molecular weight of from about 100 to about 200,000 daltons.

3. The polymeric delivery agent of claim 2 wherein the molecular weight is from 200 to about 10,000 daltons.

4. The polymeric delivery agent of claim 3 wherein the molecular weight is from about 200 to about 600 daltons.

5. The polymeric delivery agent of claim 1 wherein the polymeric delivery agent comprises units having the formula $$-(CH-C)-$$
with $R^{19}$, $R^2$, $R^1$ substituents or salts thereof where $R^1$ is a modified amino acid which is bonded to the polymer via a linkage group selected from the group consisting of —NHC(O)NH—, —C(O)NH—, —NHC(O)—, —OOC—, —COO—, —NHC(O)O—, —OC(O)NH—, —CH$_2$NH—, —NHCH$_2$—, CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond;

$R^2$ is H or —CH$_3$; and $R^{19}$ is H or —COOH.

6. The polymeric delivery agent of claim 5 wherein $R^1$ is —$R^3$—$R^4$ where $R^3$ is —NHC(O)NH—, —C(O)NH—, —NHC(O)—, —OOC—, —COO—, —NHC(O)O—, —OC(O)NH—, CH$_2$NH—, —NHCH$_2$—, —CH$_2$NHC(O)O—, —O$_2$C(O)NH—, —CH$_2$NHCOCH$_2$O—, —OCH$_2$C(O)NHCH$_2$—, —NHC(O)CH$_2$O—, —OCH$_2$C(O)NH—, —NH—, —O—, or carbon-carbon bond; and $R^4$ has the formula

[benzene ring with substituents $R^5, R^6, R^7, R^8, R^9, R^{10}$]

where $R^5$, $R^6$, $R^7$, $R^8$ and $R^9$ are independently a bond to $R^3$, or H, Cl, Br, F, —OH, —CH$_3$, —OCH$_3$, or —(CH$_2$)$_m$CH$_3$;

$R^{10}$ is a bond to $R^3$ or —COOH or —C(O)NH—$R^{11}$—$R^{12}$;

$R^{11}$ is a substituted or unsubstituted, linear or branched alkylene having a chain length of from about 1 to about 11 or —$R^{13}$—$R^{14}$—;

$R^{12}$ is a bond to $R^3$ or is —COOH, —NH$_2$, —OH, —C(O)—$R^{15}$, —COO—$R^{15}$, —NHR$^{15}$, —CR$^{15}$, Cl, or Br;

$R^{13}$ is a substituted or unsubstituted phenylene;

$R^{14}$ is a substituted or unsubstituted, linear or branched alkylene having a chain length of from about 1 to about 5;

$R^{15}$ is a bond to $R^3$; and m is from about 1 to about 4.

7. The polmeric delivery agent of claim 6 wherein $R^4$ is selected from the group consisting of

[Structure I: 2-hydroxybenzamide with alkyl chain, n=7]

(I-COOH)
[Structure: substituted benzamide with heptanoic acid chain]

II
[Structure: 2-hydroxy-N-phenylbenzamide with alkyl chain, n=3]

-continued

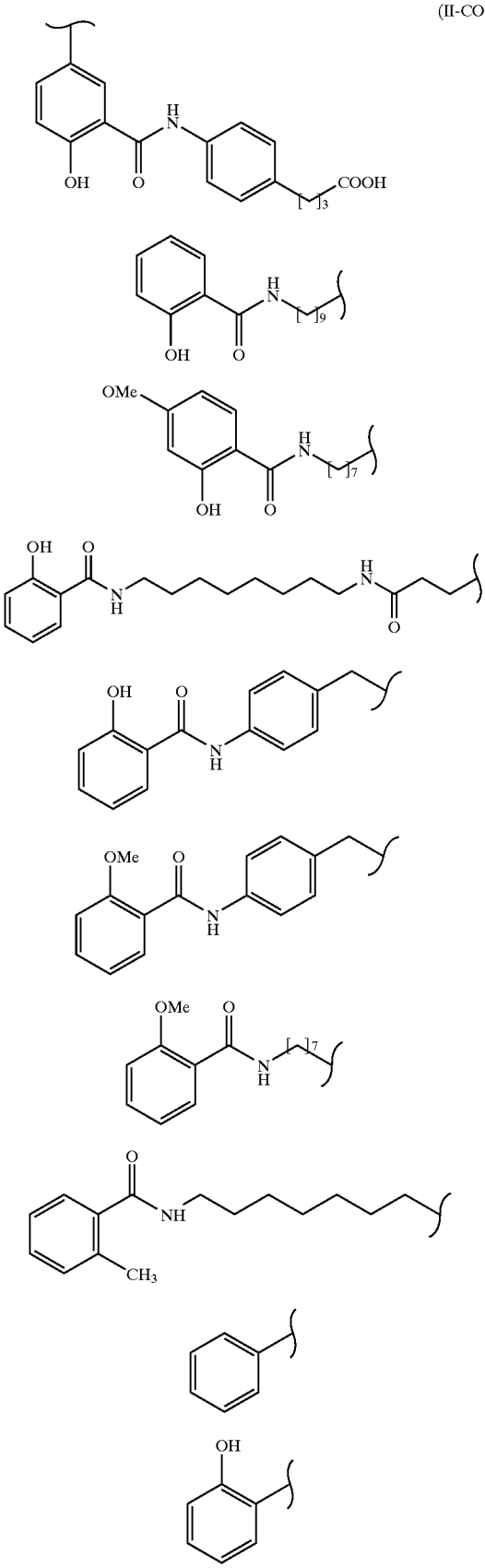

and salts thereof.

8. The polymeric delivery agent of claim 1 wherein the polymeric delivery agent comprises units having the formula:

$$R^{16}—R^{24}—CH_2CH_2—R^{17}$$

or salts thereof where $R^{16}$ is a modified amino acid which is bonded to the polymer via a linkage group selected from the group consisting of —NHC(O)NH—, —C(O)NH—, —NHC(O)—, —OOC—, —COO—, —NHC(O)O—, —OC(O)NH—, —CH$_2$NH—, —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond;

$R^{17}$ is —OH, —OCH$_3$, or —R$^{18}$;

$R^{18}$ is defined as $R^{16}$ above; and $R^{24}$ is a polymer having units of —(CH$_2$CH$_2$O)—, —CH(CH$_3$)CH$_2$O)—, or a combination thereof.

9. The polymeric delivery agent of claim 8 wherein the polymeric delivery agent comprises units having the formula:

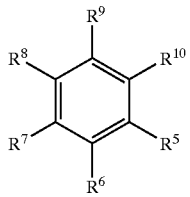

or salts thereof where $R^{23}$ is H or —CH$_3$; and n is from about 3 to about 200.

10. The polymeric delivery agent of claim 9 wherein $R^{16}$ and $R^{18}$ are independently —R$^3$—R$^4$ where $R^3$ is —NHC(O)NH—, —C(O)NH—, —NHC(O)—, —OOC—, —COO—, —NHC(O)O—, —OC(O)NH—, —CH$_2$NH—, —NHCH$_2$—, —CH$_2$NHC(O)O—, —OC(O)NHCH$_2$—, —CH$_2$NHCOCH$_2$O—, —OCH$_2$C(O) NHCH$_2$—, —NHC(O)CH$_2$O—, —OCH$_2$C(O)NH—, —NH—, —O—, or carbon-carbon bond; and $R^4$ has the formula where $R^5$, $R^6$, $R^7$, $R^8$, and $R^9$ are independently a bond to $R^3$, or H, Cl, Br, F, —OH, —CH$_3$, —OCH$_3$, or —(CH$_2$)$_m$CH$_3$;

$R^{10}$ is a bond to $R^3$ or —COOH or —C(O)NH—R$^{11}$—R$^{12}$;

$R^{11}$ is a substituted or unsubstituted, linear or branched alkylene having a chain length of from about 1 to about 11 or —R$^{13}$—R$^{14}$—;

$R^{12}$ is a bond to $R^3$ or is —COOH, —NH$_2$, —OH, —C(O)—R$^{15}$, —COO—R$^{15}$, —NHR$^{15}$, —OR$^{16}$, Cl, or Br;

$R^{13}$ is a substituted or unsubstituted phenylene;

$R^{14}$ is a substituted or unsubstituted, linear or branched alkylene having a chain length of from about 1 to about 5;

$R^{15}$ is a bond to $R^3$; and m is from about 1 to about 4.

11. The polymeric delivery agent of claim 10 wherein $R^4$ is selected from the group consisting of

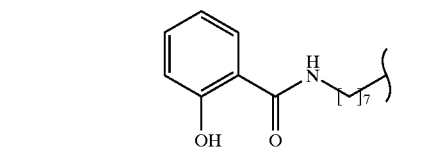

(I-COOH)

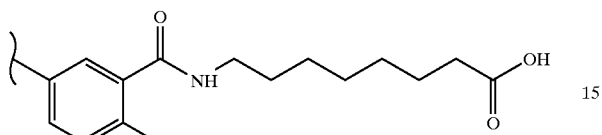

(II-COOH)

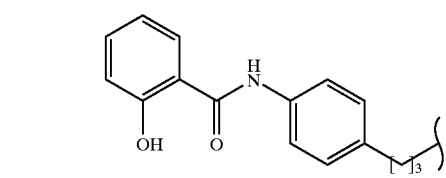

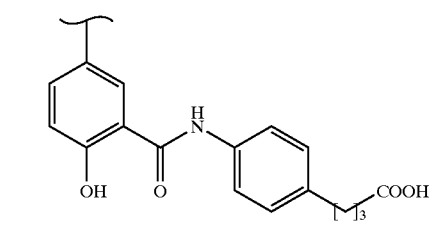

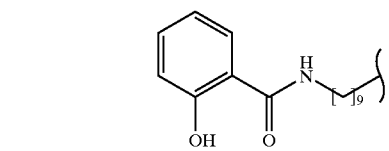

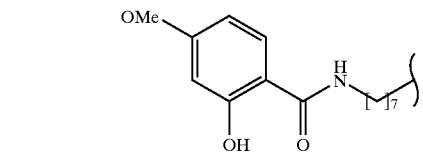

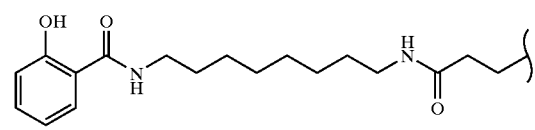

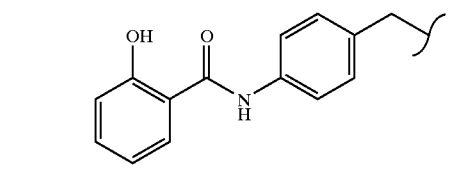

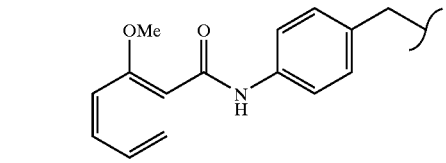

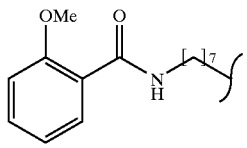

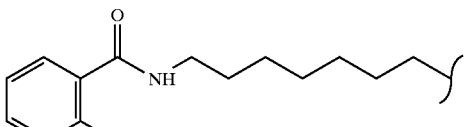

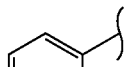

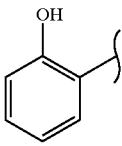

and salts thereof.

12. The polymeric delivery agent of claim 1 wherein the polymeric delivery agent comprises units having the formula:

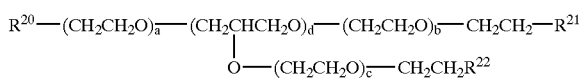

or salts thereof where $R^{20}$, $R^{21}$, and $R^{22}$ independently are H or a modified amino acid which is bonded to the polymer via a linkage group selected from the group consisting of —NHC(O)NH—, —C(O)NH—, —NHC(O)—, —OOC—, —COO—, —NHC(O)O—, —OC(O)NH—, —CH$_2$NH—, —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond;

a, b, and c independently are integers from about 1 to about 50; and d ranges from about 2 to about 10.

13. The polymeric delivery agent of claim 12 wherein $R^{20}$, $R^{21}$ and $R^{22}$ are independently —$R^3$—$R^4$ where $R^3$ is —NHC(O)NH—, —C(O)NH—, —NHC(O)—, —OOC—, —COO—, —NHC(O)O—, —OC(O)NH—, —CH$_2$NH—, —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, or carbon-carbon bond; and 4 has the formula

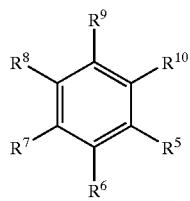

where

R⁵, R⁶, R⁷, R⁸, and R⁹ are independently a bond to R³, or H, Cl, Br, F, —OH, —CH₃, —OCH₃, or —(CH₂)$_m$CH₃;

R¹⁰ is a bond to R³ or —COOH or —C(O)NH—R¹¹—R¹²;

R¹¹ is a substituted or unsubstituted, linear or branched alkylene having a chain length of from about 1 to about 11 or —R¹³—R¹⁴—;

R¹² is a bond to R³ or is —COOH, —NH₂, —OH, —C(O)—R¹⁵, —COO—R¹⁵, —NHR¹⁵, —OR¹⁵, Cl, or Br;

R¹³ is a substituted or unsubstituted phenylene;

R¹⁴ is a substituted or unsubstituted, linear or branched alkylene having a chain length of from about 1 to about 5;

R¹⁵ is a bond to R³; and m is from about 1 to about 4.

14. The polymeric delivery agent of claim 13 wherein R⁴ is selected from the group consisting of

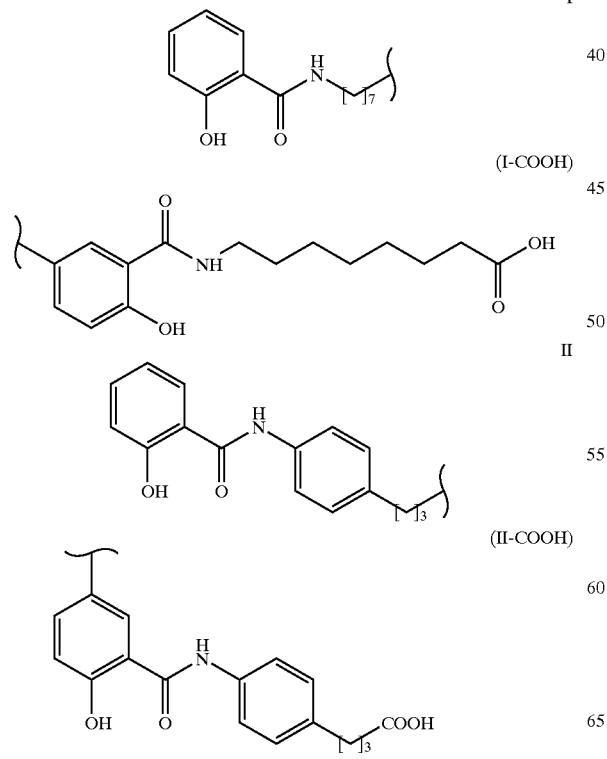

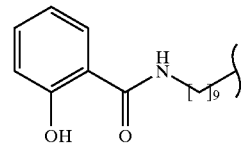

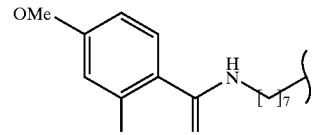

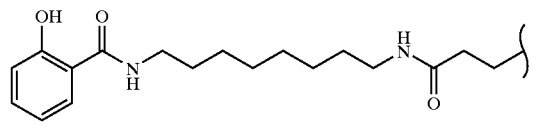

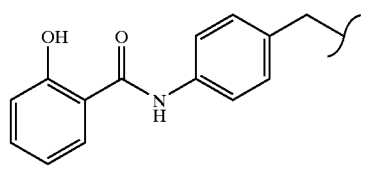

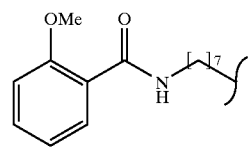

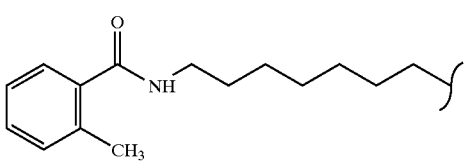

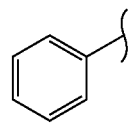

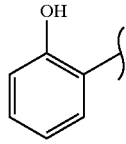

and salts thereof.

15. A composition comprising
   (a) in active agent; and
   (b) the polymeric delivery agent of claim 1.

16. A composition comprising
   (a) an active agent; and
   (b) the polymeric delivery agent of claim 5.

17. A composition comprising
(a) an active agent; and
(b) the polymeric delivery agent of claim 8.

18. A composition comprising
(a) an active agent; and
(b) the polymeric delivery agent of claim 12.

19. The composition of claim 15, wherein the active agent is selected from the group consisting of a biologically active agent, a chemically active agent, and a combination thereof.

20. The composition of claim 19, wherein the biologically active agent comprises at least one protein, polypeptide, peptide, hormone, polysaccharide, mucopolysaccharide, carbohydrate, or lipid.

21. The composition of claim 20, wherein the biologically active agent is selected from the group consisting of human growth hormone, recombinant human growth hormone, bovine growth hormone, porcine growth hormone, growth hormone-releasing hormone, an interferon, α- interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin, erythropoietin, atrial naturetic factor, an antigen, a monoclonal antibody, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, fugrastim, prostaglandins, cyclosporin, vasopressin, cromolyn sodium, soium chromoglycate, disodium chromoglycate, vancomycin, parathyroid hormone, fragments of parathyroid hormone; desferrioxamine, antimicrobials, anti-fungal agents, vitamins; analogs, fragments, mimetics and polyethylene glycol-modified derivatives of these compounds; and any combination thereof.

22. The composition of claim 21 wherein the active agent comprises insulin, unfractionated heparin, low molecular weight heparin, very low molecular weight heparin, ultra low molecular weight heparin, calcitonin, parathyroid hormone, erythropoietin, human growth hormone, recombinant human growth hormone, or combinations thereof.

23. A dosage unit form comprising:
(A) the composition of claim 15; and
(B)
  (a) an excipient
  (b) a diluent,
  (c) a disintegrant,
  (d) a lubricant,
  (e) a plasticizer,
  (f) a colorant,
  (g) a design vehicle, or
  (h) any combination thereof.

24. The dosage unit form of claim 23, comprising a tablet, a capsule, a powder, or a liquid.

25. A method for administering a biologically-active agent to an animal in need of the agent comprising orally administering to said animal the composition of claim 15.

26. A method for preparing a composition, said method comprising:
mixing:
  (A) at active agent;
  (B) the polymeric delivery agent of claim 1; and
  (C) optionally, a dosing vehicle.

27. A method for administering a biologically-active agent to an animal in need of the agent comprising intracolonically administering to said animal the composition of claim 15.

* * * * *

UNITED STATES PATENT AND TRADEMARK OFFICE
CERTIFICATE OF CORRECTION

PATENT NO. : 6,627,228 B1 Page 1 of 1
APPLICATION NO. : 09/889005
DATED : September 30, 2003
INVENTOR(S) : Sam Millstein et al.

It is certified that error appears in the above-identified patent and that said Letters Patent is hereby corrected as shown below:

Title Page #86

Please correct the filing date:

"October 10, 2001" should be --October 9, 2001--

Signed and Sealed this

Twentieth Day of March, 2007

JON W. DUDAS
*Director of the United States Patent and Trademark Office*